(12) United States Patent
Hirooka et al.

(10) Patent No.: US 6,641,539 B2
(45) Date of Patent: Nov. 4, 2003

(54) ULTRASONIC PROBE FOR OPERATION UNDER MICROSCOPE

(75) Inventors: Kenji Hirooka, Hachioji (JP); Ichiro Ohdachi, Hino (JP); Shinichi Tsutaki, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 477 days.

(21) Appl. No.: 09/732,042

(22) Filed: Dec. 7, 2000

(65) Prior Publication Data

US 2003/0045768 A1 Mar. 6, 2003

(51) Int. Cl.$^7$ ................................................. A61B 8/00
(52) U.S. Cl. ......................................................... 600/459
(58) Field of Search ................................. 600/459, 460, 600/461, 462, 104, 127, 137, 466, 117, 407

(56) References Cited

U.S. PATENT DOCUMENTS 6,004,273 A * 12/1999 Sakamoto et al. .......... 600/459
6,019,724 A    2/2000 Gronningsaeter et al.
6,036,645 A    3/2000 Drost et al.
6,039,695 A * 3/2000 Sakamoto et al. .......... 600/459
6,112,113 A * 8/2000 Van Der Brug et al. .... 600/427
6,135,946 A * 10/2000 Konen et al. ................ 600/117

* cited by examiner

*Primary Examiner*—Francis J. Jaworski
*Assistant Examiner*—Maulin Patel
(74) *Attorney, Agent, or Firm*—Scully, Scott, Murphy & Presser

(57) ABSTRACT

An ultrasonic probe for microscopic operations in accordance with the present invention consists mainly of an ultrasonic probe body, an elongated tubular member, and a bent handle member. The ultrasonic probe body has a transducer assembly attached to the distal end of a soft elongated tube that is extended from a connector to be coupled to an ultrasonic observation apparatus, and has a coupler mounted on the tube thereof. The transducer assembly and tube are passed through the elongated tubular member. The handle member is attached to the proximal end of the tubular member and includes a coupling mechanism for use in coupling the coupler to the handle member so that the coupler can be uncoupled freely.

32 Claims, 36 Drawing Sheets

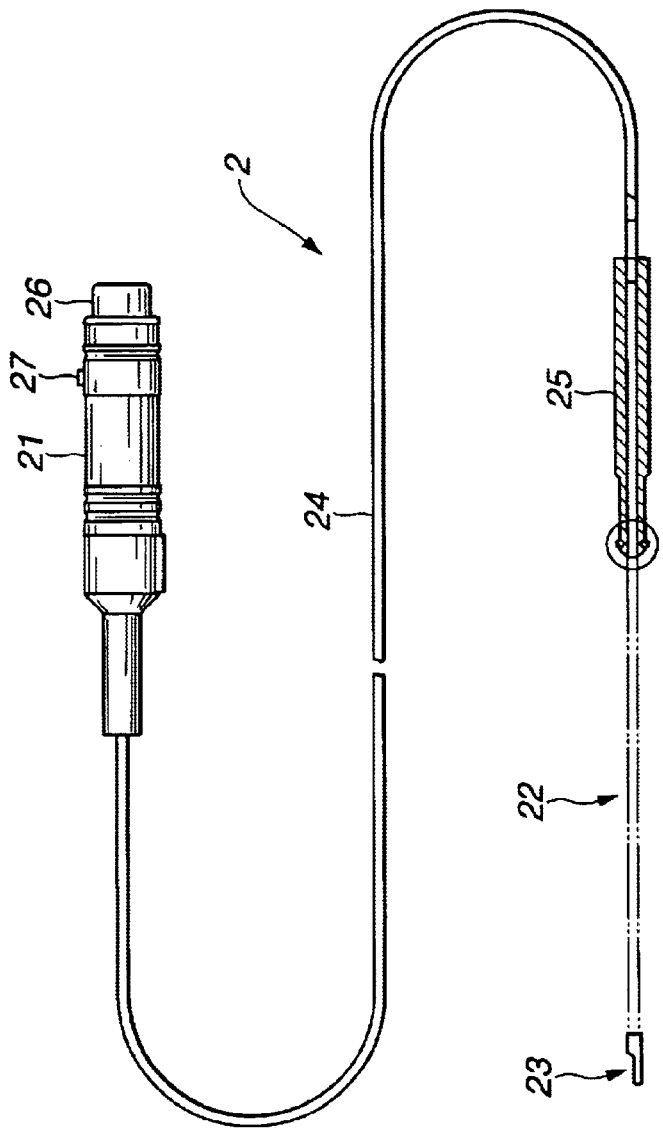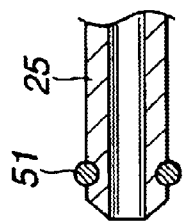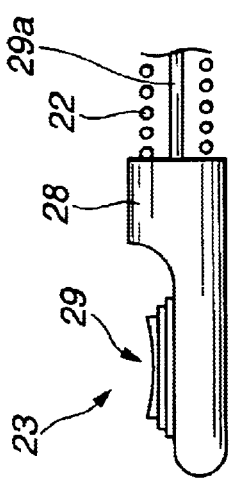

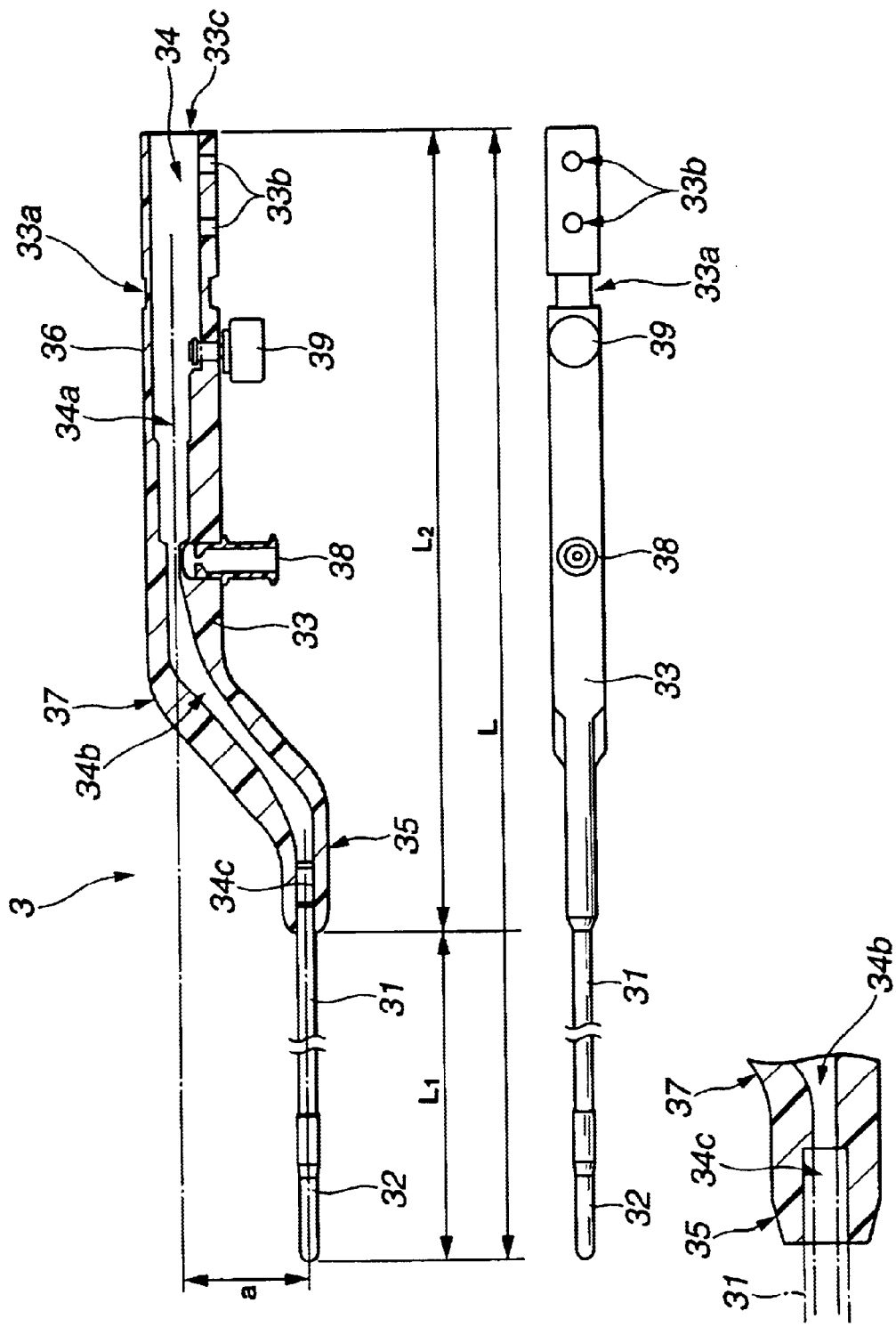

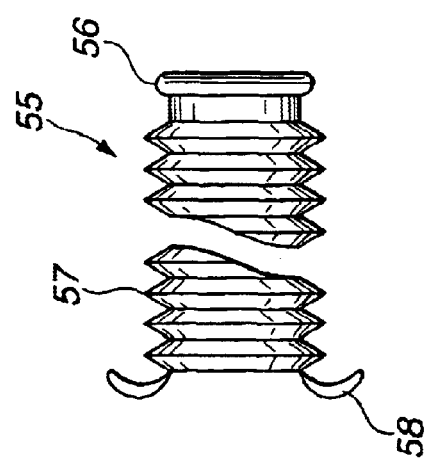
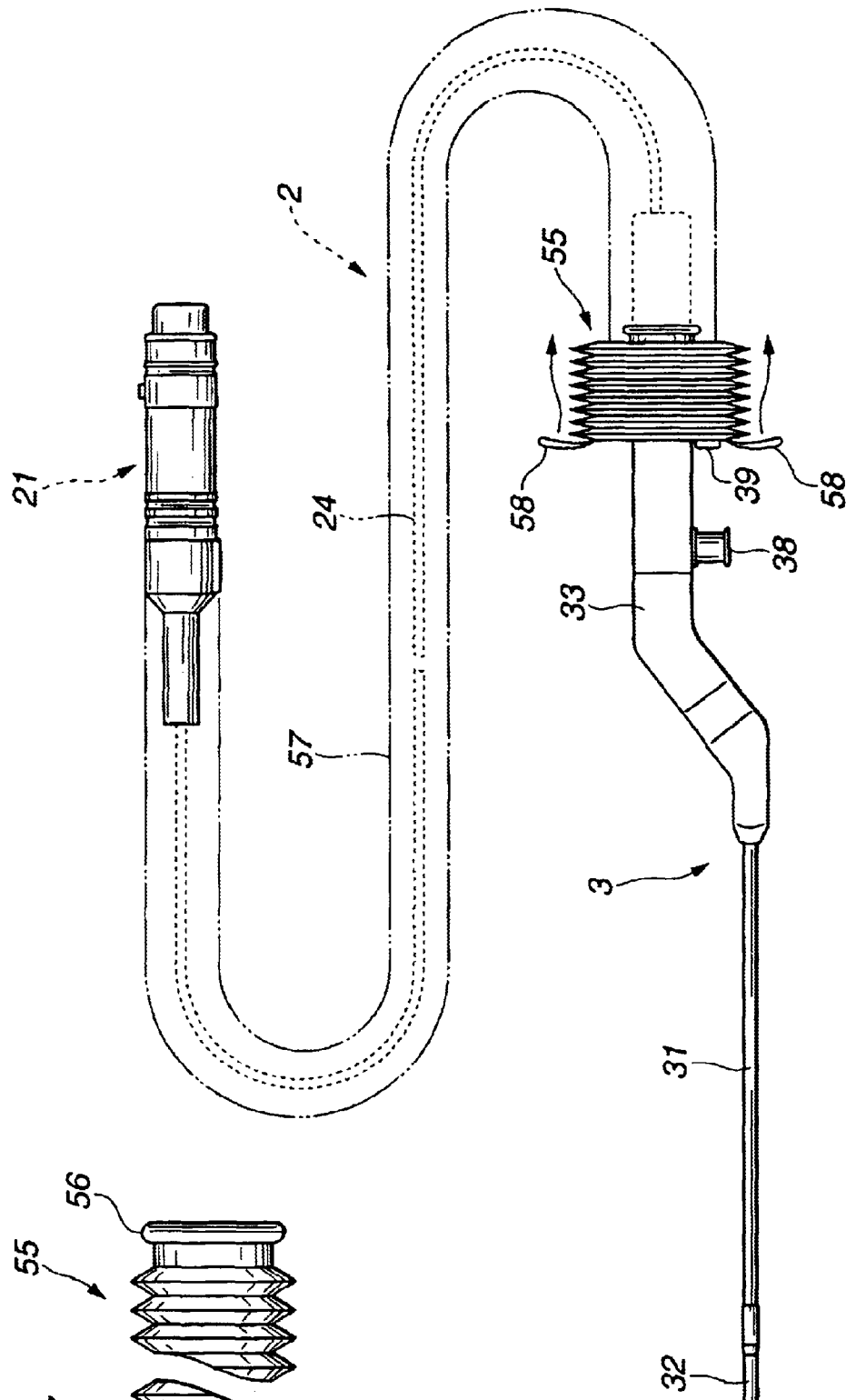

ATTACHMENT/DETACHMENT LEVER

ULTRASONIC PROBE FOR OPERATION UNDER MICROSCOPE

This application claims benefit of Japanese Application No. Hei 11-349433 filed in Japan on Dec. 8, 1999 and 2000-354846 filed in Japan on November 21 the contents of which are incorporated these references.

BACKGROUND OF THE INVENTION

1. Field of the Invention

The present invention relates to an ultrasonic probe for microscopic operations that is used under microscopic observation.

2. Description of the Related Art

In recent years, a surgery system composed of an observation/imaging apparatus and a surgical apparatus that are combined based on a region to be operated or a surgical procedure has been used in the field of medicine.

The observation/imaging apparatus includes an endoscope, a laparoscope (optical instrument), and a surgical microscope. The endoscope has a soft insertion unit inserted into a body cavity through the oral cavity or anus. The laparoscope (optical instrument) has a rigid insertion unit indwelled in the abdominal cavity using a trocar for piercing the wall of the abdominal cavity. The surgical microscope enables observation of fine nerves or vessels under magnification.

An example of medical systems is a microscopic surgery system that is a type of medical system for enabling observation of fine nerves or vessels under magnification and helping perform surgery under microscopic observation. The microscopic surgery system is employed in the field of neurosurgery. In the microscopic surgery system, a handpiece or the like is manipulated for treatment while a region concerned is observed under magnification through an eyepiece unit of a surgical microscope.

For example, when the microscopic surgery system is used to perform cerebral surgery, the surgery is performed under optical observation. It is therefore impossible to observe a deeper part of a region than an observed surface thereof during the surgery. For this reason, magnetic resonance imaging (hereinafter MRI) or computed tomography (hereinafter CT) is performed in order to produce tomographic images of the region to be treated prior to surgery.

However, even when the tomographic images depicting the region to be treated and its surroundings are produced in advance, a disadvantage of a brain shift occurs due to craniotomy. The brain shift is a phenomenon that the actual position of the brain having undergone craniotomy is different from the position thereof detected in a diagnostic image produced through CT or MRI before surgery. Moreover, some surgeons want to check a deeper part of a region than the observed surface thereof during surgery. Therefore, a ultrasonic probe for cerebral surgery or craniotomy (hereinafter, a cerebral surgery probe) or a catheter type ultrasonic probe that has a small diameter and can radiate high-frequency ultrasonic waves and offer a high resolution and high image quality is often used in combination with a surgery system during surgery.

However, when the cerebral surgery probe is used under microscopic observation, the distal part of the probe is so large in diameter that it blocks a field of view given by a microscope. For preventing the cerebral surgery probe from blocking the field of view, the cerebral surgery probe is located away from a lesion in a region to be observed, and the lesion is scanned ultrasonically. At this time, since a far point is observed, the frequency of ultrasonic waves is set to a lower value. This leads to disadvantages of a lower resolution and degraded image quality.

On the other hand, assume that the catheter type ultrasonic probe is located near a lesion under microscopic observation in order to produce high-quality images for the purpose of observation of the lesion. Since the ultrasonic probe is so soft that its maneuverability is poor, it is hard to locate the ultrasonic probe at a predetermined position under microscopic observation for the purpose of producing a desired view image.

Moreover, the ultrasonic probe that is a device employed in surgery must be sterilized prior to use. The ultrasonic probe must therefore be disposable or must be able to be autoclaved, or anyhow, sterilized.

SUMMARY OF THE INVENTION

Accordingly, an object of the present invention is to provide an ultrasonic probe for microscopic operations capable of being sterilized and being manipulated excellently under microscopic observation.

Another object of the present invention is to provide an ultrasonic probe for microscopic operations capable of producing ultrasonic images that are very helpful in observing a lesion.

Briefly, according to the present invention, there is provided an ultrasonic probe for microscopic operations comprising an ultrasonic probe body, an elongated tubular member, and a bent handle member. The ultrasonic probe body has a transducer assembly attached to the distal end of a soft elongated tube that is extended from a connector to be coupled to an ultrasonic observation apparatus. The ultrasonic probe body has a coupler mounted on the tube. The transducer assembly and tube are passed through the elongated tubular member. The bent handle member is attached to the proximal end of the tubular member and has a coupling mechanism for use in coupling the coupler to the handle member so that the coupler can be uncoupled freely.

BRIEF DESCRIPTION OF THE DRAWINGS

FIG. 1 to FIG. 9 are concerned with the first embodiment of the present invention;

FIG. 1 is an explanatory diagram schematically showing the configuration of a microscopic surgery system;

FIG. 2A to FIG. 2C are explanatory diagrams showing the components of an ultrasonic probe body;

FIG. 2A shows the ultrasonic probe body;

FIG. 2B is an explanatory diagram showing the components of a transducer assembly;

FIG. 2C is an explanatory diagram showing the structure of the distal part of a stepped base;

FIG. 3A and FIG. 3B are explanatory diagrams showing the components of an observation body;

FIG. 3A is a sectional view and bottom view for explaining the structure and components of the observation body;

FIG. 3B is an explanatory diagram showing a pipe placement hole in a pipe placement portion;

FIG. 4A shows an example of a structure enabling the distal cap to be freely detachably attached to the linkage pipe;

FIG. 4B shows distal caps capable of being freely detachably attached to the linkage pipe;

FIG. 4C shows an observed state of a region with a distal cap, which suits for a thin lumen, attached to the linkage pipe;

FIG. 4D shows an observed state of a region with a distal cap, which suits for a thick lumen, attached to the linkage pipe;

FIG. 5A and FIG. 5B are explanatory diagrams showing a sterilization cover;

FIG. 5A is an explanatory diagram showing the components of the sterilization cover;

FIG. 5B is an explanatory diagram concerning the operation of the sterilization cover;

FIG. 6 is an explanatory diagram showing an ultrasonic probe for microscopic operations;

FIG. 7 is an explanatory diagram showing an examined state of a region;

FIG. 8A shows an observation body;

FIG. 8B is an 8B—8B sectional view of the ultrasonic probe body shown in FIG. 8A;

FIG. 8C shows an ultrasonic image displayed on a screen of a monitor;

FIG. 9 is an explanatory diagram showing an example of the structure of an ultrasonic probe for microscopic operations capable of being easily oriented in any direction;

FIG. 10A to FIG. 11B are concerned with the second embodiment of the present invention;

FIG. 10A to FIG. 10E are explanatory diagrams showing another example of an observation body;

FIG. 10A shows a practical structure of an observation body;

FIG. 10B is an explanatory diagram concerning the operation of the observation body;

FIG. 10C is an explanatory diagram showing an example of application of the observation body;

FIG. 10D is a 10D—10D sectional view of the observation body shown in FIG. 10C;

FIG. 10E is an explanatory diagram concerning the operation of the observation body shown in FIG. 10C;

FIG. 11A and FIG. 11B are explanatory diagrams showing an example of application of the observation body shown in FIG. 10A to FIG. 10E;

FIG. 11A is an explanatory diagram showing the observation body having a bending member;

FIG. 11B is an explanatory diagram showing an example of the structure of the bending member;

FIG. 12 is an explanatory diagram showing the components of a microscopic probe having a differently structured observation body;

FIG. 13 is an explanatory diagram concerning the operation of the microscopic probe;

FIG. 14A is an explanatory diagram showing a handle member;

FIG. 14B is an explanatory diagram showing a probe passage member;

FIG. 14C is an explanatory diagram showing the observation probe body;

FIG. 14D is a sectional view of the observation probe body;

FIG. 14E is an explanatory diagram showing the structure of a flexible shaft placed in a base placement portion;

FIG. 15 is an explanatory diagram showing the structure of the distal part of a microscopic probe;

FIG. 16 is a perspective view showing the distal part of the microscopic probe;

FIG. 17 is an explanatory diagram showing a range scanned with the microscopic probe;

FIG. 22 to FIG. 24 are concerned with an example of application of the fourth embodiment;

FIG. 22 is an explanatory diagram showing an example of a structure for minimizing an artifact;

FIG. 23 shows the appearance of the microscopic probe;

FIG. 24A to FIG. 34C are explanatory diagrams showing another example of the structure for minimizing an artifact;

FIG. 24A is a front view of a reflecting mirror surface;

FIG. 25 to FIG. 29B are concerned with the fifth embodiment of the present invention;

FIG. 25 is an explanatory diagram showing another example of the components of an ultrasonic probe body;

FIG. 26A shows the ultrasonic probe body having a pipe portion thereof extended substantially parallel to the centerline (axis) of an uneven linkage portion;

FIG. 26B shows the ultrasonic probe body having a pipe portion thereof bent relative to the centerline (axis) of an uneven linkage portion;

FIG. 27 is an explanatory diagram showing the components of a microscopic probe;

FIG. 28 is an explanatory diagram showing another example of a locking base;

FIG. 29A and FIG. 29B are explanatory diagrams showing another examples of a transducer assembly;

FIG. 29A shows a transducer assembly having transducer elements arranged in a convex form;

FIG. 29B shows a transducer assembly having transducer elements arranged in a linear form;

FIG. 30A is an explanatory diagram showing a structure having an observation optical system incorporated in a radial scanning type transducer assembly;

FIG. 30B is an explanatory diagram showing a structure having an observation optical system incorporated in a convex scanning type transducer assembly;

FIG. 30C is an explanatory diagram showing a structure having an observation optical system incorporated in a linear scanning type transducer assembly;

FIG. 31A is an explanatory diagram showing a structure having a treatment transducer incorporated in addition to an observation transducer;

FIG. 31B is an explanatory diagram showing a structure for producing a three-dimensional ultrasonic view image;

FIG. 32 is an explanatory diagram showing an example of application of an observation body included in the electronic ultrasonic probe for microscopic operations;

FIG. 33 is an explanatory diagram showing an example of a structure for improving the performance of the observation body enabling observation;

FIG. 34 and FIG. 35 are explanatory diagrams showing an example of a structure included in an ultrasonic probe for microscopic operations having a balloon;

FIG. 34 is an explanatory diagram showing a structure having a balloon attached to an observation body;

FIG. 35A shows a dilated balloon;

FIG. 35B shows the balloon whose internal pressure has risen to discharge an ultrasound propagating medium to outside;

FIG. 39A is an explanatory diagram showing the structure of a base placement portion having an elastic member mounted therein;

FIG. 39B is an explanatory diagram concerning the operation of the base placement portion having the elastic member mounted therein;

FIG. 40A to FIG. 42 are explanatory diagrams showing an example of a configuration for improving the performance of an electronic ultrasonic probe for microscopic operations enabling observation;

FIG. 40A and FIG. 40B are explanatory diagrams showing the relationship between a handle member and a navigation body head;

FIG. 40A shows the navigation body head mounted on an operating table;

FIG. 40B shows the navigation body head;

FIG. 41 is an explanatory diagram showing a maker member attached to an observation body;

FIG. 42 is an explanatory diagram showing an example of a view image displayed on the screen of a monitor;

FIG. 43A is an explanatory diagram showing an example of a structure including a cutter; and FIG. 43B is an explanatory diagram showing the structure whose cutter is driven to rotate.

DESCRIPTION OF THE PREFERRED EMBODIMENTS

Embodiments of the present invention will be described with reference to the drawings below.

Referring to FIG. 1 to FIG. 9, the first embodiment of the present invention will be described below.

Figure 1:
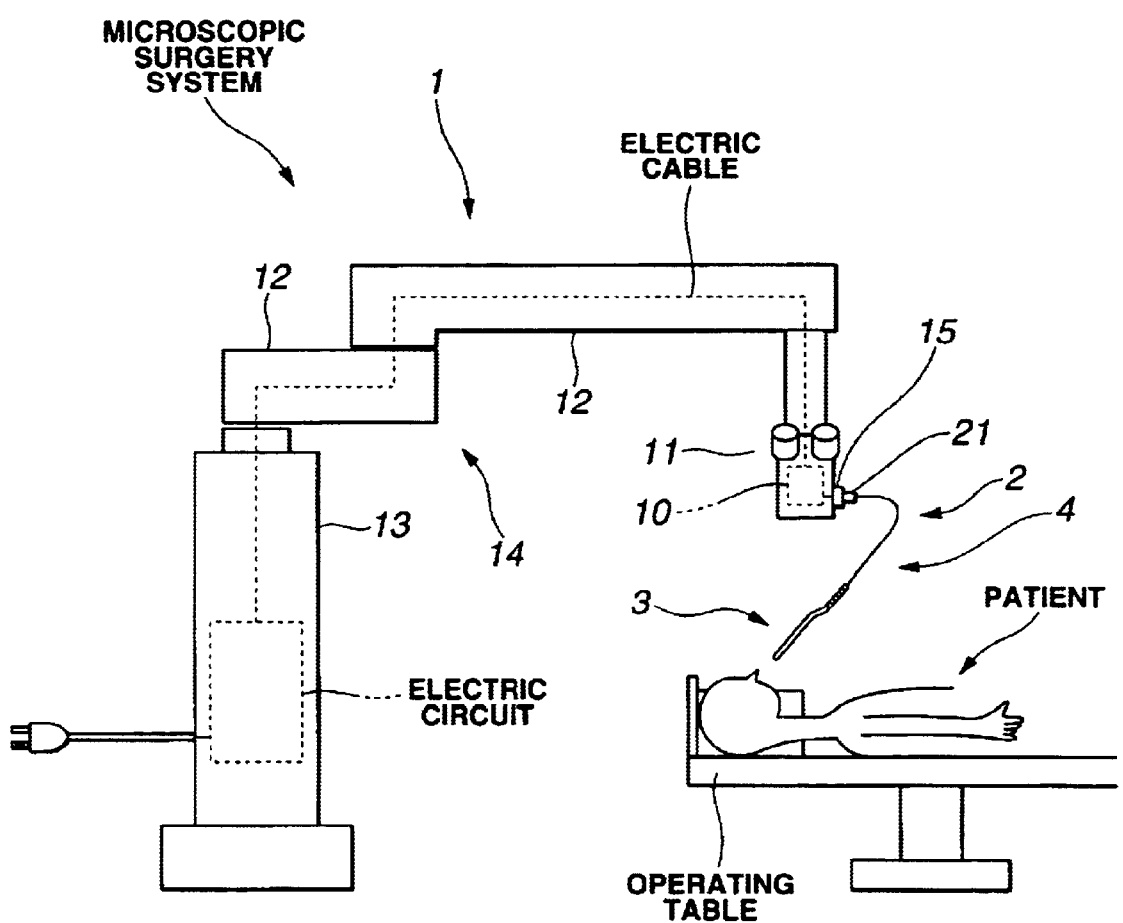

A surgery system in accordance with the present embodiment shown in FIG. 1 is a microscopic surgery system consisting mainly of a surgical microscope 1 used to observe a region to be treated and various apparatuses used to treat or examine the region to be treated. The surgical apparatuses include surgical appliances such as clamp forceps and a knife, various surgical devices such as a motor-driven cautery, an ultrasonic knife, and an electric cautery, and an observation device such as an ultrasonic probe.

The surgical microscope 1 consists mainly of a microscope eyepiece unit 11 (hereinafter, an eyepiece unit) and an arm stand 14. The eyepiece unit 11 enables observation under magnification of a region to be treated of a patient lying down on an operating table, and is disposed freely to lie near the patient. The arm stand 14 consists of a support arm 12 and a support 13 and enables three-dimensional movement and tilting of the eyepiece unit 11.

A motor and a probe drive unit 10 are incorporated in the arm stand 14. The motor is used to drive and rotate a housing, which will be describe later, included in an ultrasonic probe for microscopic operations (hereinafter, a microscopic probe) 4 composed of an ultrasonic probe body 2 and an observation body 3. The probe drive unit 10 includes an ultrasound originating/receiving circuit and drives an ultrasonic transducer, which will be described later, held in the housing.

Moreover, an electric probe joint (hereinafter, a probe joint) 15 is formed on the wall of the arm stand 14 near the eyepiece unit 11. A connector 21 of the ultrasonic probe body 2 included in the microscopic probe 4 is coupled to the probe joint 15 so that the connector 21 can be uncoupled freely. When the connector 21 is coupled to the probe joint 15, the microscopic probe 4 and probe drive unit 10 are mechanically and electrically connected to each other.

Figure 7:
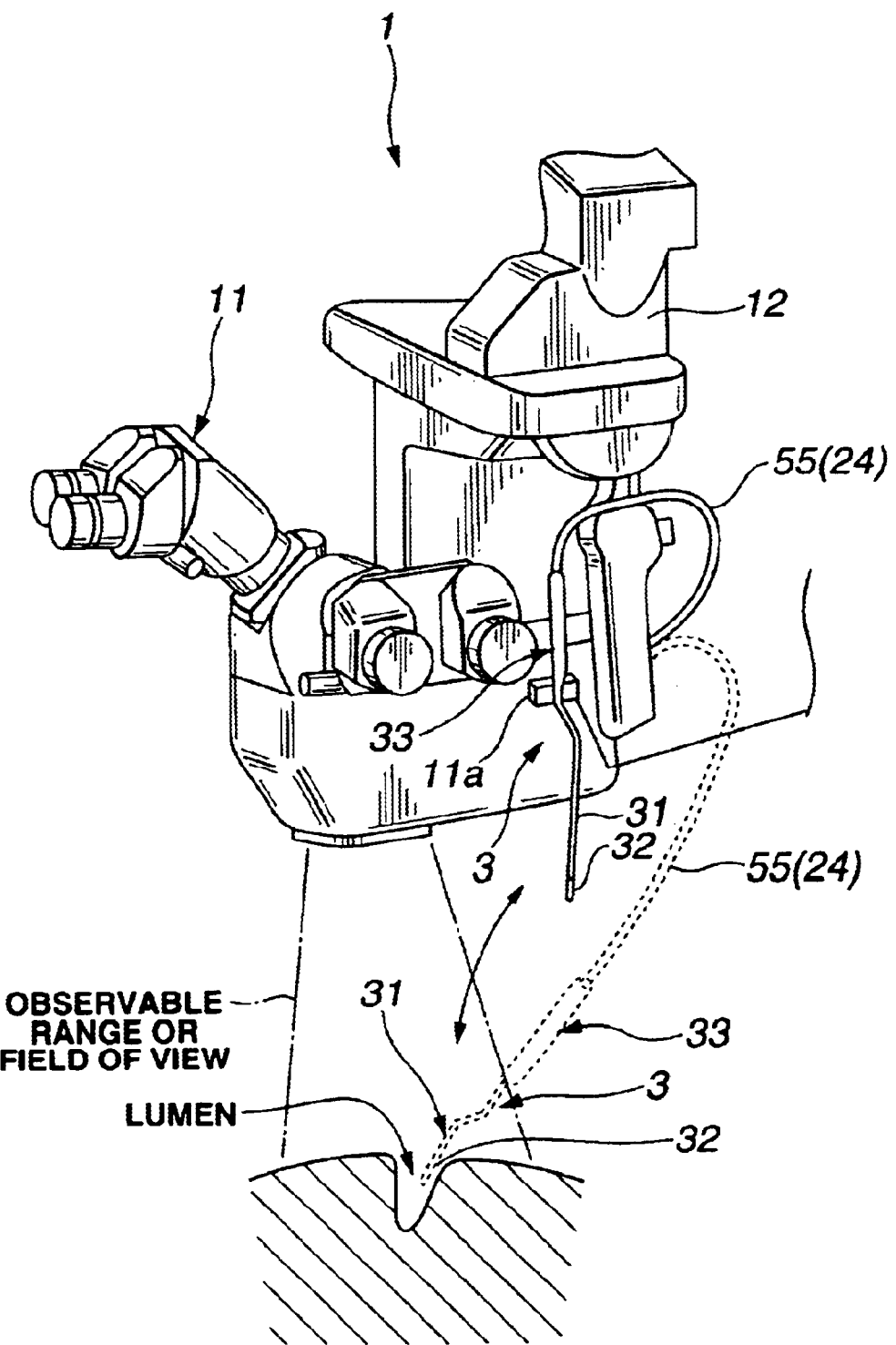

Aside from the probe joint 15, a plurality of electric joints through which power is fed to various surgical apparatuses and a sterilized probe holder 11a in FIG. 7 can be freely detachably attached to the arm stand 14. A handle member 33 in FIG. 3 of the microscopic probe 4 is mounted in the probe holder 11a so that it can be dismounted freely.

An electric circuit serving as a voltage transformer is incorporated in the support 13. The electric circuit is electrically connected to the electric joints over electric cables.

Referring to the drawings, the components of the microscopic probe 4 will be described by taking a practical example.

To begin with, the ultrasonic probe body 2 will be described with reference to FIG. 2A to FIG. 2C.

The ultrasonic probe body 2 shown in FIG. 2A consists mainly of the connector 21, an elongated flexible shaft 22, a transducer assembly 23, a soft tube member 24, and a stepped base 25. The connector 21 is mechanically and electrically attached to the probe drive unit 10. The flexible shaft 22 conveys driving torque exerted by the motor, which is not shown, incorporated in the probe drive unit 10 through the connector 21. The transducer assembly 23 is located at the distal end of the flexible shaft 22. The tube member 24 has a proximal end thereof locked in the connector 21 and shields the proximal half of the flexible shaft 22. The stepped base 25 that is a base member is fixed to the distal end of the tube member 24 and realized with, for example, a metallic pipe. The stepped base 25 serves as a coupler for coupling the ultrasonic probe body to the observation body 3.

The connector 21 has a linkage cylinder 26 and a pin 27. The linkage cylinder 26 serves as a conveyor for conveying driving force exerted by the probe drive unit 10 to the flexible shaft 22. The pin 27 is used to hold the connector 21. The flexible shaft 22 is enclosed in the tube member 24 so that it can be rotated freely.

As shown in FIG. 2B, the transducer assembly 23 located at the distal end of the flexible shaft 22 consists of a housing 28 fixed to the tip of the flexible shaft 22 and an ultrasonic transducer 29 held in the housing 28. A signal line 29a lies through the flexible shaft 22. The ultrasonic transducer 29 is electrically connected to an ultrasound originating/receiving circuit or the like incorporated in the probe drive unit 10 over the signal line 29a. In short, the microscopic probe 4 in accordance with the present embodiment is designed to scan a plane orthogonal to a direction of insertion of the probe so as to produce a so-called radial image.

As shown in FIG. 2C, an O ring 51 is mounted on the distal part of the stepped base 25 in order to seal a base placement hollow, which will be described later, in a watertight manner.

Next, the observation body 3 will be described with reference to FIG. 3.

As shown in FIG. 3A, the observation body 3 consists mainly of a straight pipe 31, an ultrasound transmissive cap (which may be referred to as a distal cap) 32, and a handle member 33. The straight pipe 31 is an elongated straight linkage pipe realized with, for example, a hard resin member. The distal cap 32 is realized with a resin member made of polyethylene or polymethyl pentane that transmits ultrasonic waves. The distal cap 32 has a space in which the housing 28 attached to the distal end of the straight pipe 31 is placed. The handle member 33 is located at the proximal end of the straight pipe 31, bent, and realized with, for example, a bent transparent resin member. The handle member 33 has a penetrating hollow 34 through which the housing 28 and flexible shaft 22 included in the ultrasound probe body 2 are passed.

The distal cap 32 is fixed to the straight pipe 31 as an integral part of the straight pipe 31 through bonding or bobbin winding bonding. Otherwise, an elastic member 52 such as an O ring is mounted on the periphery of the distal part of the straight pipe 31, and the distal part of the straight pipe 31 is enclosed in the proximal part of the distal cap 32. Thus, the distal cap 32 is freely detachably attached to the straight pipe 31 while having the space thereof sealed in a watertight manner.

Figure 4A:
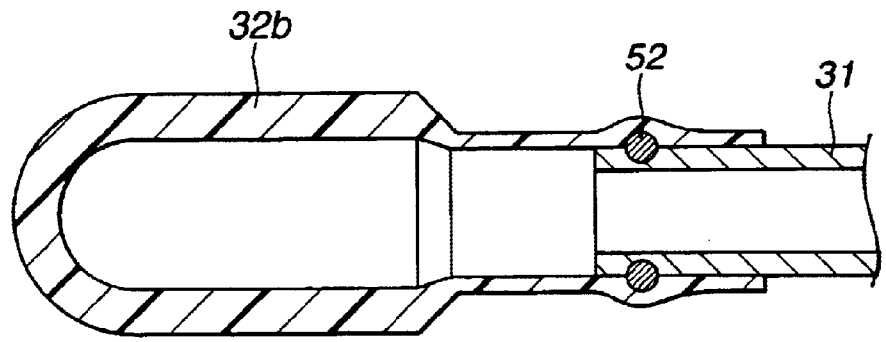
FIG. 4A to FIG. 4D are explanatory diagrams concerning the relationship between distal caps and a linkage pipe.
Figure 4B:
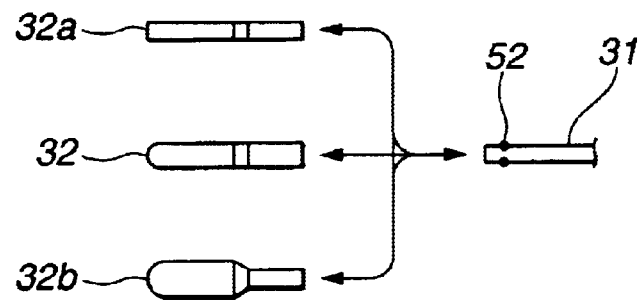

As shown in FIG. 4B, distal caps having mutually different outer diameters can be selectively attached to the end of the straight pipe 31. For example, the distal cap 32 that is short, a thin distal cap 32a fit for a region to be observed having a small-diameter lumen, and a thick distal cap 32b fit for a region to be observed having a large-diameter lumen can be selectively attached to the end of the straight pipe 31.

Figure 4C:
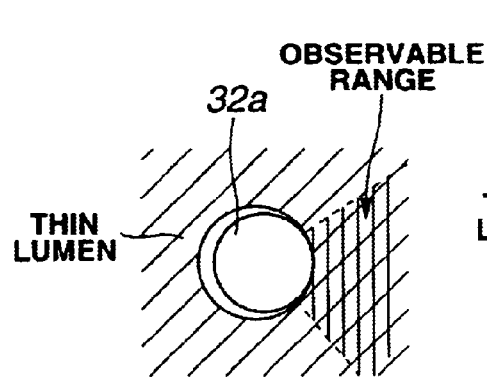
Figure 4D:
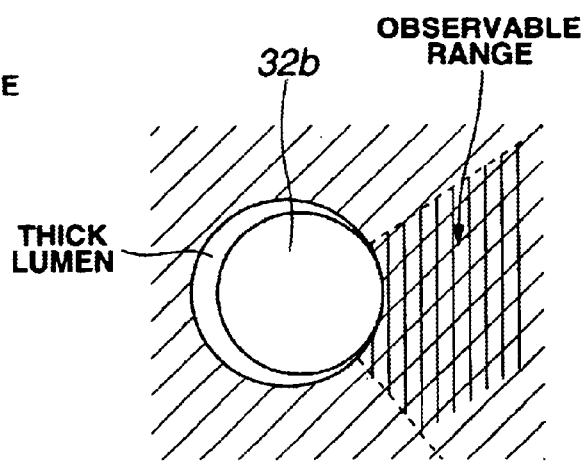

As shown in FIG. 4C and FIG. 4D, the distal caps 32, 32a, and 32b can be used selectively according to the size of a lumen of a region to be observed. Consequently, a clearance created in a lumen around the distal cap 32, 32a, or 32b is minimized to prevent the distal cap 32, 32a, or 32b from vibrating during observation. Eventually, excellent ultrasonic view images can be produced.

The bent handle member 33 shown in FIG. 3A consists of a pipe placement portion 35, a base placement portion 36, and an uneven linkage portion 37. The straight pipe 31 is placed in the pipe placement portion 35. The stepped base 25 is placed in the base placement portion 36 that also serves as a hand-held portion. The uneven linkage portion 37 links the base placement portion 36 and pipe placement portion 35.

The penetrating hollow 34 of the handle member 33 consists of a pipe placement hollow (see FIG. 3B) 34c, a base placement hollow 34a, and a sloping hollow 34b that are joined smoothly. The pipe placement hollow 34c is bored in the pipe placement portion 35, and the proximal part of the straight pipe 31 is locked in the pipe placement hollow 34c. The base placement hollow 34a is bored in the base placement portion 36, and the stepped base 25 is placed in the base placement hollow 34a. The sloping hollow 34b is bored in the uneven linkage portion 37, and links the pipe placement hollow 34c and base placement hollow 34a.

The centerline (axis) of the pipe placement hollow 34c bored in the handle member 33 and the centerline (axis) of the base placement hollow 34a bored therein are made uneven.

With the straight pipe 31 locked in the pipe placement hollow 34c, the straight pipe 31 and base placement portion (hand-held portion) 36 of the handle member 33 are uneven with a distance a between them.

The length and weight of the observation body 3 will be described below.

When the surgical microscope 1 is used to perform surgery, a distance from an objective to a region to be observed (referred to as a working length) is about 300 mm. The overall length L of the observation body 3 employed in the present embodiment is made smaller than the working length.

Specifically, according to the present embodiment, a distance L1 from the distal end of the handle member 33 to the distal end of the distal cap 32 fixed to the hard pipe 31 is set to 120 mm. Moreover, the length L2 of the handle member 33 is set to 130 mm. The overall length L of the observation body 3 is therefore 250 mm. The magnitude of unevenness between the straight pipe 31 and the base placement portion 36 of the handle member 33, that is, the distance a is set to 20 mm.

On the other hand, the weight of the observation body 3 is set to a range from 50 g to 10 g in consideration of an incident that part of the distal cap 32 may touch a lesion and a weight balance. Namely, when the observation body 3 has an adequate weight, even if such an incident should occur, the incident will be accurately communicated to an operator. Moreover, the weight of the observation body 3 must be balanced with the weights of the other components in terms of maneuverability.

Moreover, reference numeral 38 denotes a fluid injection portion 38. An ultrasound propagating medium is injected into the space in the distal cap 32 through the fluid injection port 38 by way of the sloping hollow 34b, pipe placement hollow 34c, and the hollow of the straight pipe 31. The ultrasound propagating medium is a fluid whose acoustic impedance is close to that of a living body, for example, deaerated water, physiological saline, sterilized water, or ultrasonic jelly. Reference numeral 39 denotes a body locking screw that is a locking member for locking and holding the stepped base 25 placed in the base placement hollow 34a.

The inner diameter of the base placement hollow 34a is determined so that an O ring 51 mounted on the distal part of the stepped base 25 will come into close contact with the wall of the base placement hollow 34a to seal the base placement hollow 34a in a watertight manner. At the same time, the stepped base 25 must be able to slide within the base placement hollow 34a for placement. Consequently, an ultrasound propagating medium injected through the fluid injection port 38 is prevented from flowing out to an operator's hand through a proximal opening 33c of the base placement portion 36 after passing through a clearance between the wall of the base placement hollow 34a and the periphery of the stepped base 25.

Moreover, a peripheral groove 33a and a sensor mount 33b are formed on the periphery of the proximal part of the base placement portion 36 of the handle member 33. The distal end of a sterilization cover (see FIG. 5A) to be described later is fitted in the peripheral groove 33a. A position-of-probe body checking sensor, for example, the one 135 shown in FIG. 41 and described later is mounted on the sensor mount 33b. Owing to the position checking sensor, an indication of the position of the probe can be seen together with an ultrasonic image within the field of view of the microscope.

As shown in FIG. 5A, the sterilization cover 55 is elongated and realized with a soft member. The sterilization cover 55 consists of an elastic stationary part 56, a contractile and expandable bellows 37, and a knob 58. The elastic stationary part 56 is shaped substantially like an O ring and fitted in the peripheral groove 33a. The knob 58 is held to stretch the pleated bellows 57.

As shown in FIG. 5B, the sterilized sterilization cover 55 is attached to the handle member 33 with the elastic stationary part 56 thereof fitted in the peripheral groove 33a. At this time, the bellows 57 is pleated and the knob 58 is facing the distal cap 32. In this state, the ultrasonic probe body 2 is placed in the handle member 33 as indicated with dashed lines. The knob 58 of the sterilization cover 55 is pulled in a direction of an arrow. Consequently, the bellows 57 is turned inside out, and the inner surface of the bellows 57 becomes the outer surface thereof. The bellows 57 thus shields the tube member 24 as indicated with alternate long and two short dashes lines.

In other words, when the microscopic probe 4 is in use, a portion of the ultrasonic probe body 2 from the distal end thereof at which the transducer assembly 23 is located to the middle point of the tube member 24 is placed in the observation body 3. A portion of the tube member 24 from the middle point thereof to the proximal end thereof is sheathed with the bellows 57 of the sterilization cover 55.

Consequently, the ultrasonic probe body 2 need not be sterilized or cleaned at every completion of surgery. Even when the ultrasonic probe body 2 is used once, once the sterilized observation body 3 having the sterilization cover 55 attached thereto is mounted on the ultrasonic probe body 2, the microscopic probe 4 can be used in a sterilized state.

According to the present embodiment, the straight pipe 31, distal cap 32, and handle member 33 are sterilizable and disposable. This means that the observation body 3 is of a disposable type.

The handle member 33 and straight pipe 31 may be formed as a united body using a resin member. Moreover, the distal cap 32 may be detachable from the straight pipe 31. This leads to drastic improvement of the efficiency in cleaning or sterilizing the hollows of the straight pipe 31 and handle member 33 after use. When this structure is adopted, the handle member 33 and straight pipe 31 may be designed to be of a reusable type and resistive to autoclaving.

The operations of the microscopic probe 4 having the foregoing components will be described below.

Figure 6:
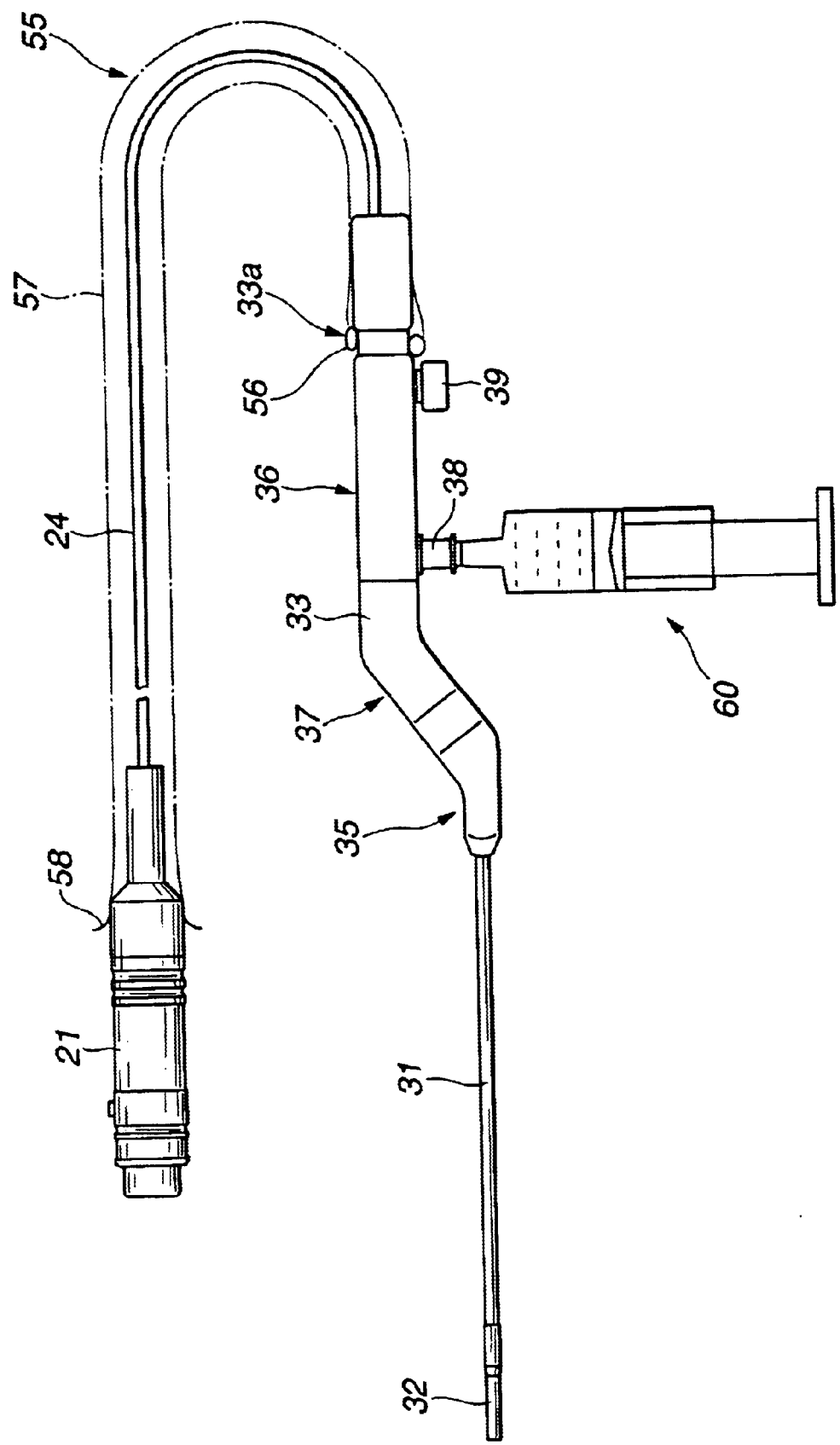

As shown in FIG. 6, the ultrasonic probe body 2 and observation body 3 are joined as a united body to construct the microscopic probe 4.

At this time, first, the housing 28 fixed to the distal end of the flexible shaft 22 included in the ultrasonic probe body 2 is inserted through the proximal opening 33c of the handle member 33. The housing 28 is then passed through the penetrating hollow 34 and the hollow of the straight pipe 31, and routed to the space in the distal cap 32. The penetrating hollow 34 is composed of the base placement hollow 34a, sloping hollow 34b, and pipe placement hollow 34c. In this state, the stepped base 24 is placed in the base placement hollow 34.

As mentioned above, the handle member 33 is realized with a transparent resin member. The passage of the housing 28 through the base placement hollow 34a, sloping hollow 34b, and pipe placement hollow 34c can be visually checked. An amount of force to be exerted for insertion or a direction of insertion can be adjusted properly. The housing 28 can be advanced smoothly and routed readily but will not be abutted on the wall of the penetrating hollow 34 with strong force.

Thereafter, the stepped base 25 inserted into the base placement hollow 34a is thrust forward against constraining force exerted by the O ring 51. When the ultrasonic transducer 29 reaches a predetermined position in the space of the distal cap 32, the body locking screw 39 is tightened to abut on the stepped base 25. Consequently, the stepped base 25 is fixed to the handle member 33. The ultrasonic probe body 2 and observation body 3 are thus joined as a united body to construct the microscopic probe 4.

Thereafter, the knob 58 of the sterilization cover 55 sterilized and fitted in the peripheral groove 33a is pulled forwards in order to sheath the tube member 24 with the bellows 57 as indicated with dot-dash lines.

Thereafter, an injector 59 to which deaerated water is poured halfway is coupled to the fluid injection port 38. The penetrating hollow 34, the hollow of the straight pipe 31, and the space in the distal cap 32 are deaerated. After air in the observation body 3 is fully deaerated, the deaerated water is injected into the penetrating hollow 34 using the injector 59.

If the deaerated water does not flow into the space in the distal cap 32, the distal cap 32 is swung several times. This causes the deaerated water to flow into the distal cap 32 due to the operation of centrifugal force.

An operator places the distal cap 32 of the microscopic probe 4 indicated with dashed lines in FIG. 7 at a predetermined position within a lumen located within an observable range or the field of view of the eyepiece unit 11 of the surgical microscope 1. As illustrated, the microscopic probe 4 is held in the probe holder 11a with the distal cap 32 thereof oriented vertically downwards. The distal cap 32 is used while always being oriented vertically downwards during examination. Therefore, once water flows into the space in the distal cap 32, no bubble will occur in the distal cap 32 during examination.

After examination is completed, the body locking screw 39 is loosened, and the stepped base 25 is removed from the handle member 33. The flexible shaft 22 of the ultrasonic probe body 2 and the transducer assembly 23 thereof are pulled out of the observation body 3. The used observation body 3 is disposed of, and the sterilized observation body 3 is mounted on the ultrasonic probe body 2. Preparations are then made for a subsequent examination.

As mentioned above, the handle member included in the observation body is realized with a hard member and bent. The centerline (axis) of the pile placement hollow bored in the handle member and the centerline (axis) of the base placement hollow bored therein are made uneven. Therefore, when the linkage pipe is locked in the pipe placement hollow, the distal cap fixed to the distal end of the linkage pipe and the base placement portion of the handle member are held uneven by a predetermined distance. Consequently, the distal cap or ultrasound transmissive cap enclosing the transducer assembly of the microscopic probe can be readily located at a position optimal for an intended region. At this time, the field of view defined by the eyepiece unit of the surgical microscope will not be blocked.

Consequently, the ultrasound transmissive cap enclosing the transducer assembly can be located at a position optimal for an intended region whenever an operator desires it. An ultrasonic image enjoying a high resolution can be produced instantaneously.

Incidentally, according to the present embodiment, the ultrasonic probe body and the observation body are separate bodies. Alternatively, they may be constructed as a united body. Nevertheless, their fundamental functions are drawn out.

Moreover, the housing 28 enclosed in the distal cap 32 of the observation body 3 is rotated with rotation of the flexible shaft 22. Specifically, driving torque exerted by the motor included in the probe drive unit 10 incorporated in the arm stand 14 of the surgical microscope 1 is conveyed over the flexible shaft 22 to rotate the housing 28. It is therefore hard to accurately detect the position of the rotating housing 28 and to grasp a positional relationship at the sight of an ultrasonic image displayed on the screen of a monitor.

A structure described below is adopted so that the position of the rotating transducer assembly 23 can be detected in order to display an ultrasonic image, which helps readily grasp a positional relationship, on the screen of the monitor.

Figure 8A:
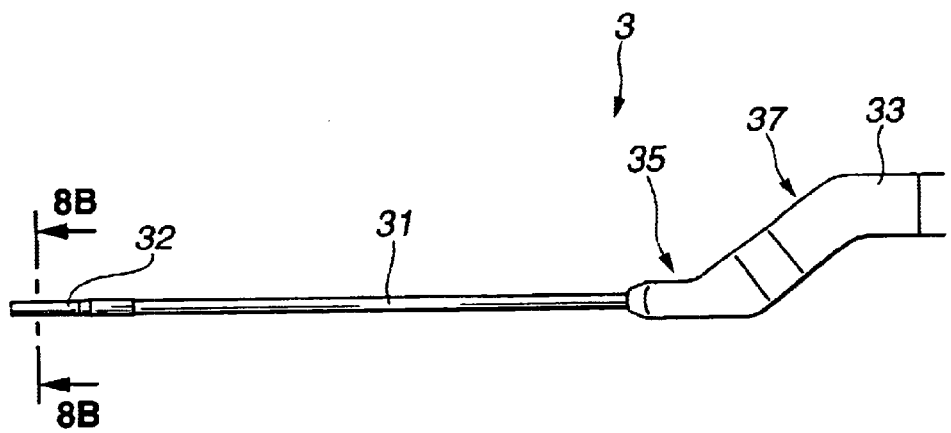
FIG. 8A to FIG. 8C are explanatory diagrams showing a variant of an ultrasound transmissive cap.
Figure 8B:
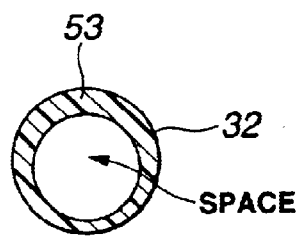

As shown in FIG. 8A and FIG. 8B, the thickness of the distal cap 32 may not be uniform but part of the distal cap 32 may be formed as a thick part 53. Alternatively, the center point on the inner diameter of the cap may not be aligned with the center point on the outer diameter thereof. The distal cap 32 may thus be structured to have a non-uniform thickness.

When the transducer assembly 23 is rotated within the distal cap 32, multiple echoes are detected through the thick part of the distal cap 32. Namely, multiple echoes are depicted as shown in FIG. 8C on an ultrasonic image.

A direction-of-rotation correcting means and an ultrasound originating/receiving circuit are included in the probe drive unit 10 so that a direction from which multiple echoes are returned will always remain constant (from above in the drawing). When the distal cap 32 is attached to the straight pipe 31 of the observation body 3, the thick part 53 is oriented in a specific direction, for example, oriented towards the uneven linkage portion 37.

Figure 8C:
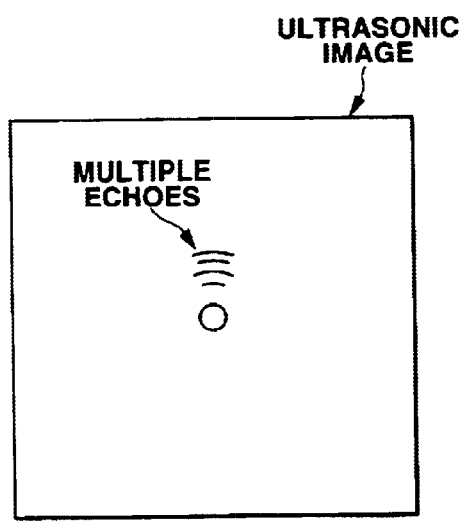

Consequently, as shown in FIG. 8C, multiple echoes are visualized on the screen of the monitor so that they will be seen returned from above all the time. This helps an operator observe a lesion while readily grasping the positional relationship between components of the handle member 33 and the positional relationship between things depicted in an ultrasonic image.

The distal cap is structured in order to utilize multiple echoes. Therefore, an error in the position of the distal cap a direction of rotation thereof caused by the flexible shaft can be corrected and an image can be oriented in a desired direction easily.

Figure 9:
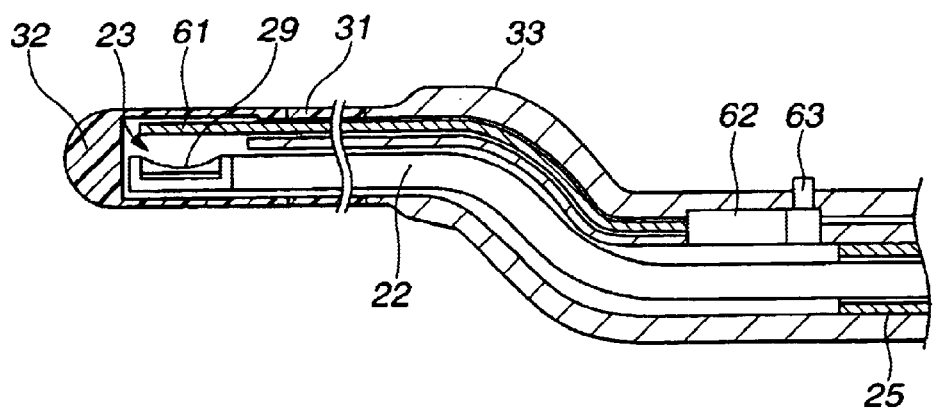

As shown in FIG. 9, a reflector 61 may be included so that it can be freely thrust or sunk relative to the radiating surface of the ultrasonic transducer 29. The reflector 61 is located in front of the radiating surface of the ultrasonic transducer 29 when needed. Thus, an ultrasonic image of the reflector 61 is displayed on the screen of the monitor. This helps orient the distal cap. As a means for advancing or withdrawing the reflector 61, an advancing/withdrawing mechanism may be constructed with a linear motor 62 and a switch 63, which is manipulated, located as shown in FIG. 9. Otherwise, the reflector 61 may be moved manually.

Referring to FIG. 10A to FIG. 11B, the second embodiment of the present invention will be described below.

Figure 10A:
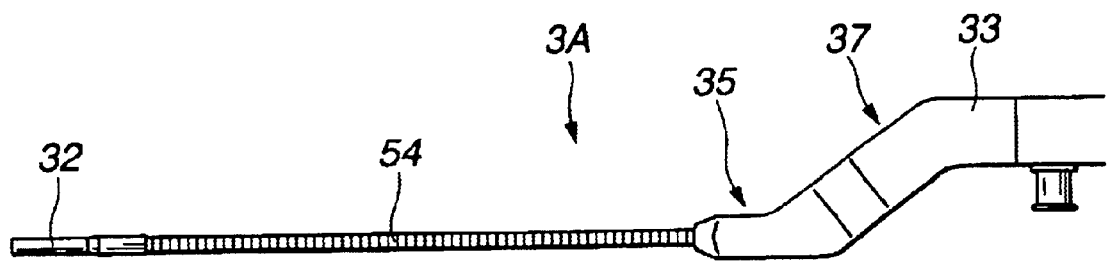
Figure 10B:
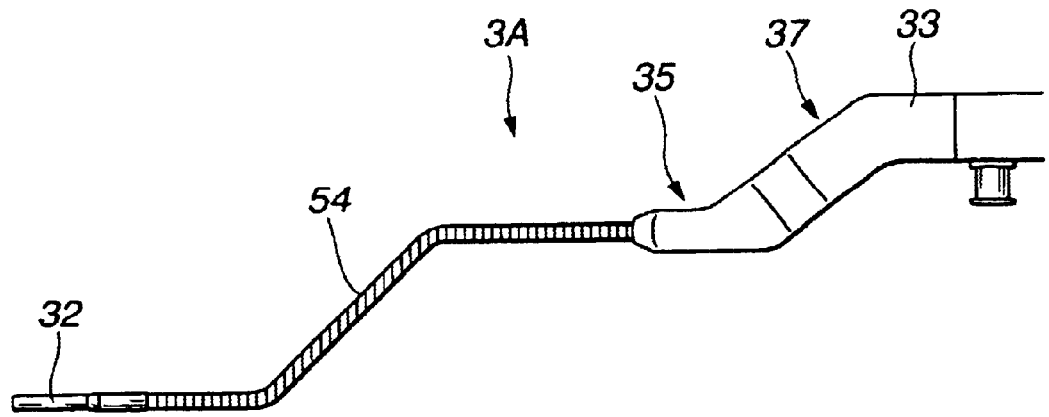

As shown in FIG. 10A, according to the present embodiment, a bellows pipe 54 hollowed and freely bent and held bent as shown in FIG. 10B is substituted for the straight pipe 31 that is straight and links the distal cap 32 and handle member 33. The bellows pipe 54 is used as a linkage pipe, thus constructing an observation body 3A. The other components are identical to those of the first embodiment. The same reference numerals are assigned to the identical components, and the description of the components is omitted.

The bellows pipe 54 of the observation body 3A is initially shaped straight as shown in FIG. 10A. In this state, the transducer assembly 23 and flexible shaft 22 of the ultrasonic probe body 2 are inserted into the observation body 3A. After the transducer assembly 23 and flexible shaft 22 are placed at their predetermined positions, the observation body 3A and ultrasonic probe body 2 are joined as a united body using the body locking screw 39 in order to construct the microscopic probe 4. An ultrasound propagating medium is injected using the injector 59. Thereafter, the bellows pipe 54 is, as shown in FIG. 10B, bent according to the shape of a lumen of a region having a lesion.

As mentioned above, the linkage pipe of the observation body is realized with the bellows pipe capable of being bent and held bent. The bent state of the bellows pipe can be varied depending on the shape of a lumen of a region having a lesion. Consequently, ultrasonic images representing the areas in the region located in various angular directions can be produced. The other operations and advantages are identical to those of the first embodiment.

Figure 10C:
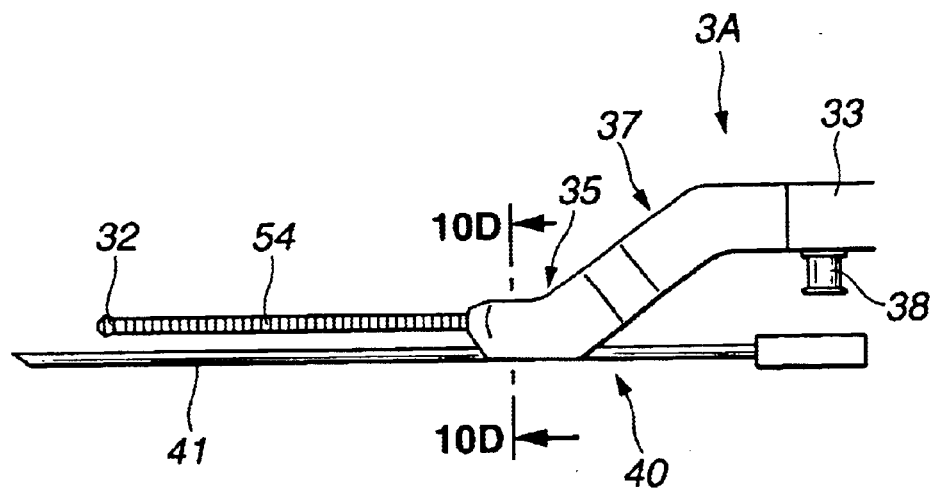
Figure 10D:
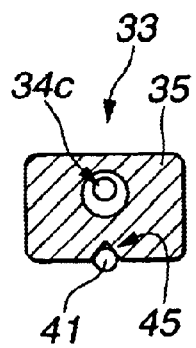
Figure 10E:
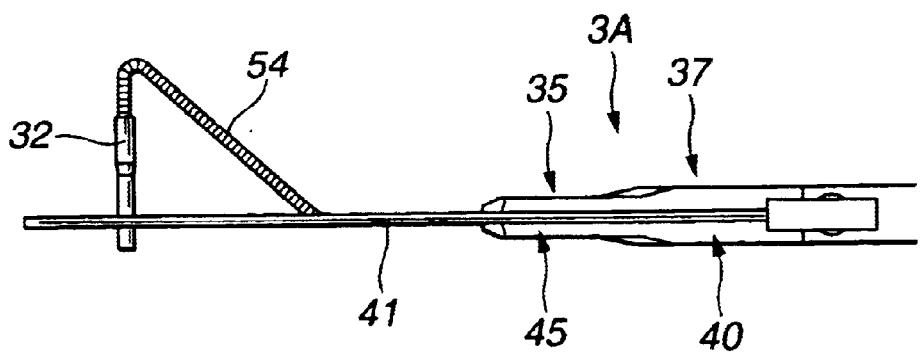

The bellows pipe 54 structured as shown in FIG. 10C may be bent as shown in FIG. 10E so that the distal cap 32 will be located orthogonally to a direction of insertion. In this case, the orientation of the distal cap 32 is adjusted so that an ultrasonic image representing an area in a region located in the direction of an extension of the inserted microscopic probe. A needle groove 45 in which a needle portion 41 of a puncturing needle 40 is put is bored in the pipe placement portion 35 of the handle member 33 so that the needle groove 45 will extend in the direction of insertion. The needle portion 41 of the puncturing needle 40 is shot under ultrasonic guidance in order to inject an agent into a lesion or collect the tissue of a lesion.

As mentioned above, when the linkage pipe of the observation body is realized with the bellows pipe capable of being bent freely and held bent, a lesion can be punctured safely under ultrasonic guidance.

Figure 11A:
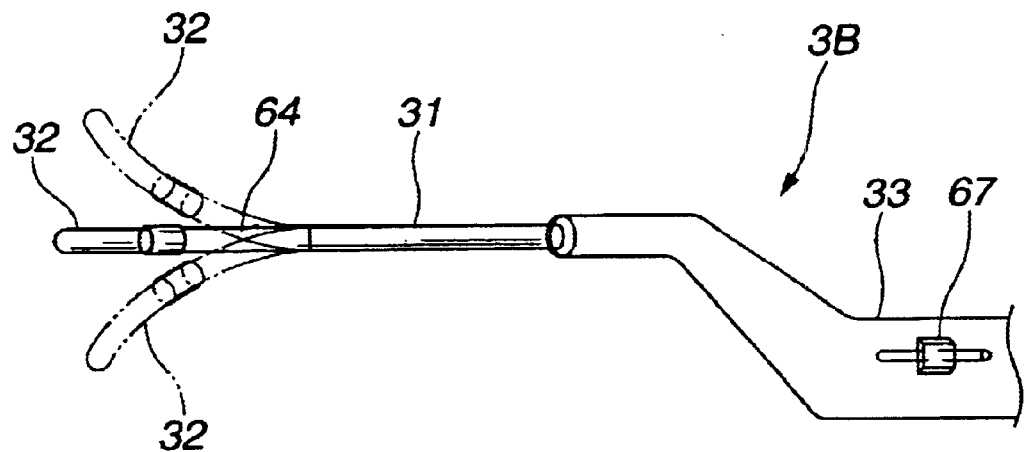
Figure 11B:
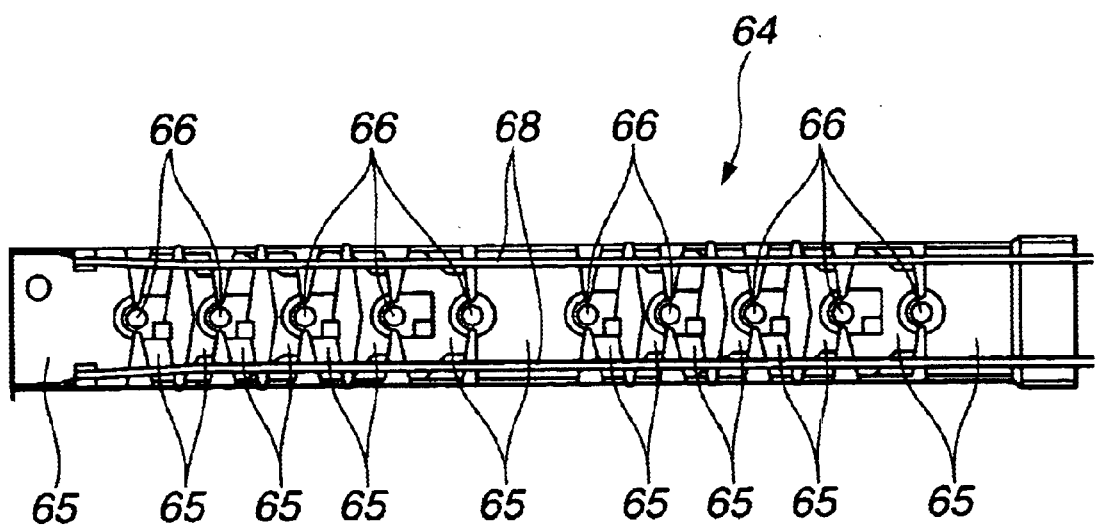

A bending member 64 structured as shown in FIG. 11B and angled vertically as indicated with dashed lines in FIG. 11A and laterally alike may be substituted for the straight pipe 31 or may be formed as part of the straight pipe 31. An observation body 3B having the bending member 64 may be constructed. The bending member 64 is composed of a plurality of bending pieces 65 which are concatenated using rivets 66 so that the bending pieces can turn freely. Angling wires 68 to be hauled by manipulating a sliding angling lever 67 formed at a predetermined position are coupled to the distal bending piece 65.

Consequently, the angling lever 67 is manipulated in order to angle the bending member 64 in line with the shape of a lumen of a region having a lesion. Thus, ultrasonic images representing the areas in the region located in various directions can be produced. The bending member 64 has the concatenated bending pieces 65 sheathed with a rubber bending tube that is not shown.

Figure 12:
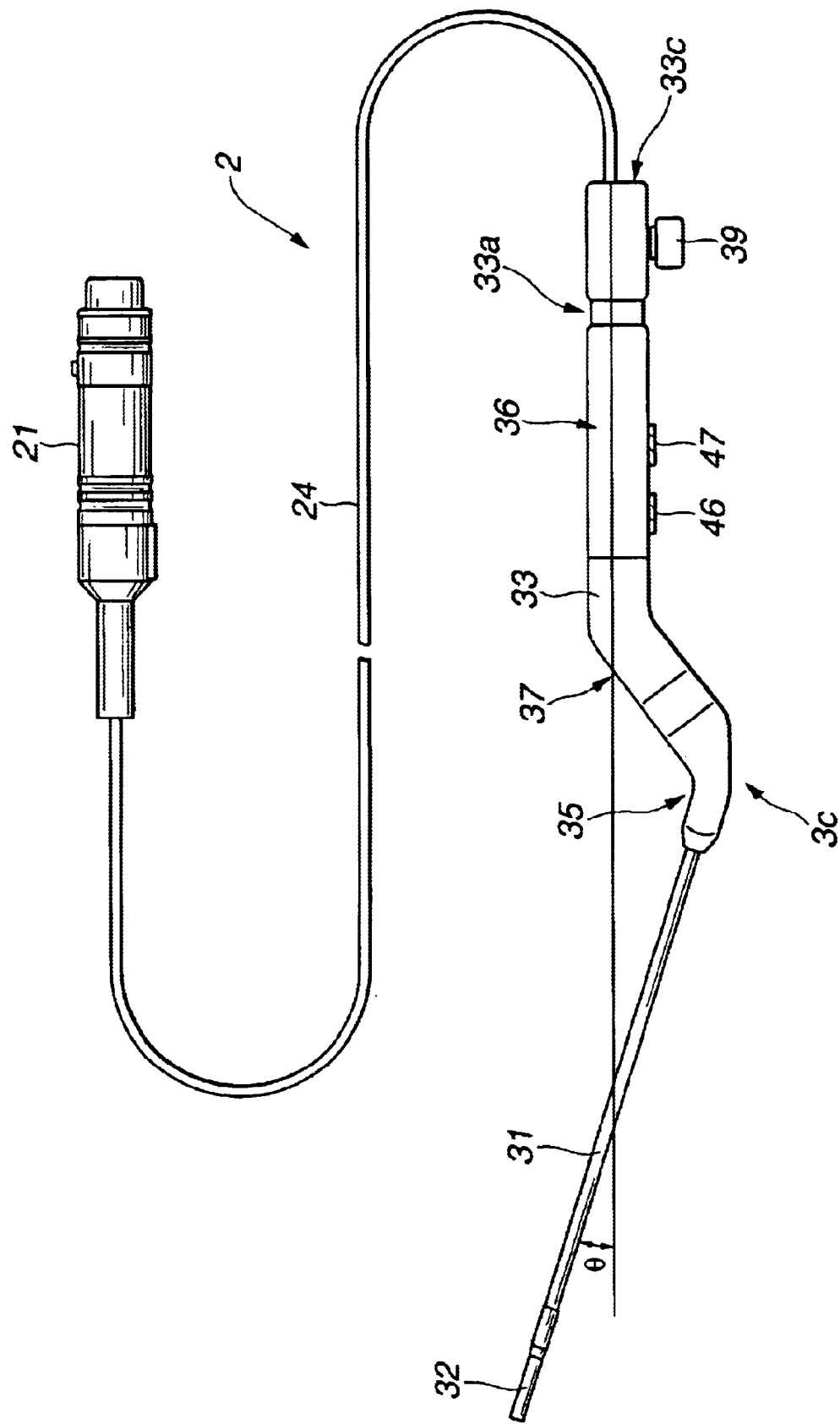
FIG. 12 and FIG. 13 are concerned with the third embodiment of the present invention.
Figure 13:
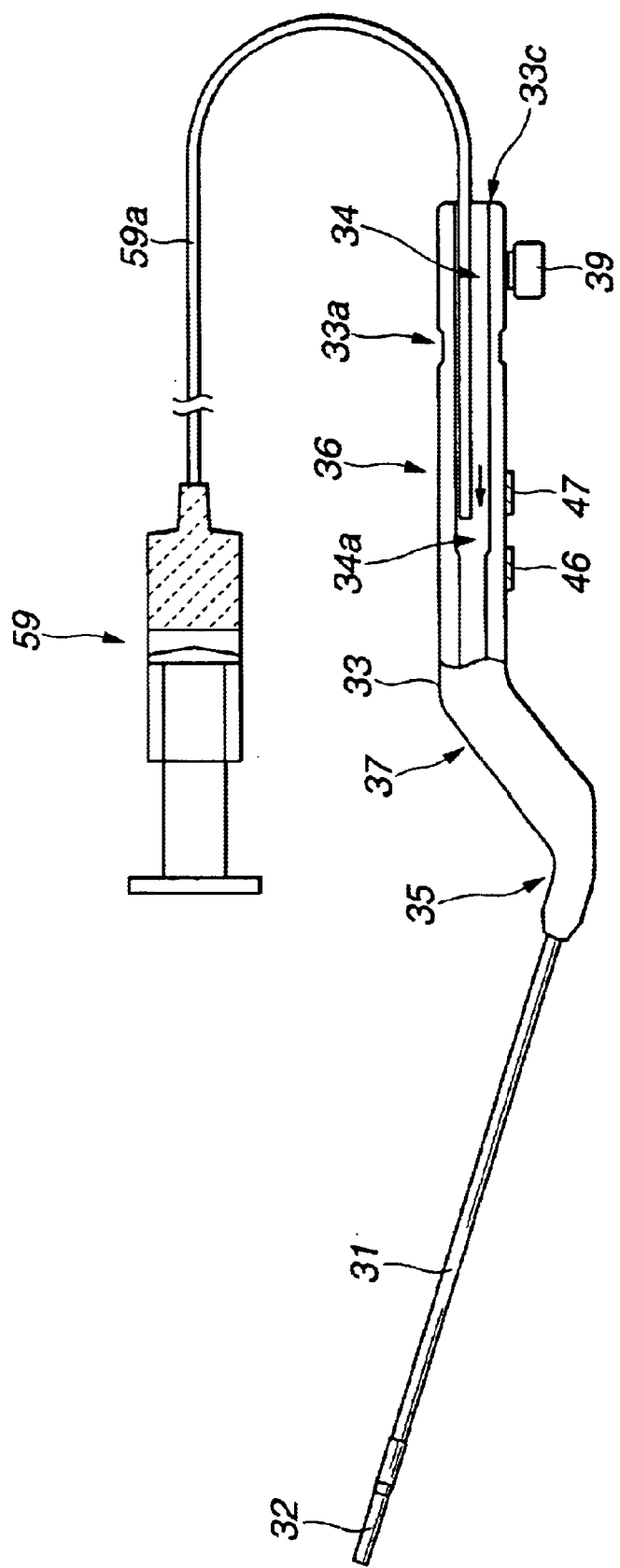

Referring to FIG. 12 and FIG. 13, the third embodiment of the present invention will be described below.

As shown in FIG. 12, an observation body 3C employed in the present embodiment does not include the fluid injection port 38 that is formed on the lateral surface of the handle member 33 employed in the first and second embodiments. The proximal opening 33c of the handle member 33 is also used as the fluid injection port. Moreover, the body locking screw 39 is located proximally beyond the peripheral groove 33a in which the distal part of the sterilization cover 55 is fitted.

Furthermore, a remote switch 46 used to freeze an ultrasonic image and a remote switch 47 used to give control to print out an ultrasonic image are bared on the lateral surface of the handle member 33 included in the observation body 3C.

The handle member 33 included in the observation body 3C is realized with a hard member, and bent so that the centerline (axis) of the straight pipe 31 and the centerline of the base placement portion (hand-held portion) 36 will meet at an angle θ. The distal cap 32 fixed to the distal end of the straight pipe 31 and the base placement portion 36 of the handle member 33 are made uneven.

A magnitude of unevenness of the handle member 33 is determined for each operator in consideration of a balance of the handle member held by an operator, maneuverability thereof, and a field of view ensured by the microscope. Besides, excellent maneuverability must be offered without the sacrifice of the basic function of the handle member. Incidentally, the sterilization cover is not shown for a clear understanding of the structure of the observation body.

According to the present embodiment, for injecting deaerated water into the space in the distal cap 32, a small-diameter tube 59a coupled to the injector 59 is, as shown in FIG. 13, placed in the penetrating hollow 34. The injector 59 has deaerated water poured thereinto.

The small-diameter tube 59a of the injector 59 is passed through the penetrating hollow 34, and the tip of the small-diameter tube 59a is routed to the space in the distal cap 32. The deaerated water is then injected. An amount of injected deaerated water is determined to be a bit smaller than the volume of the space in the observation body 3C.

After the injection of the deaerated water is completed, the transducer assembly 23 and flexible shaft 22 of the ultrasonic probe body 2 are moistened with water and then inserted into the penetrating hollow 34 through the proximal opening 33c of the handle member 33. Since the flexible shaft 22 is moistened with water, air hardly enters the deaerated water injected into the space within the observation body 3C.

After the flexible shaft 22 is inserted, the stepped base 25 placed in the base placement hollow 34a is thrust against constraining force exerted by the O ring 51. When the stepped base 25 reaches a predetermined position, the body locking screw 39 is tightened. Eventually, the ultrasonic probe body 2 and observation body 3C are joined as a united body to construct the microscopic probe 4. The other components are identical to those of the aforesaid embodiments. The same reference numerals are assigned to the identical components, and the description of the components is omitted.

As mentioned above, the fluid injection portion is excluded from the handle member. The remote switches used to instruct various movements are included in the handle member. This leads to drastically improved maneuverability. The other operations and advantages are identical to those of the aforesaid embodiments.

Referring to FIG. 14A to FIG. 14E, an example of application of the observation body shown in FIG. 12 and FIG. 13 will be described below.

Figure 14A:
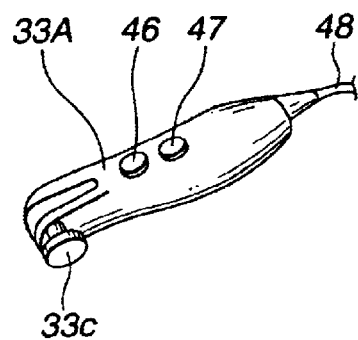
FIG. 14A to FIG. 14E are explanatory diagrams showing an example of application of the observation probe body shown in FIG. 12.
Figure 14B:
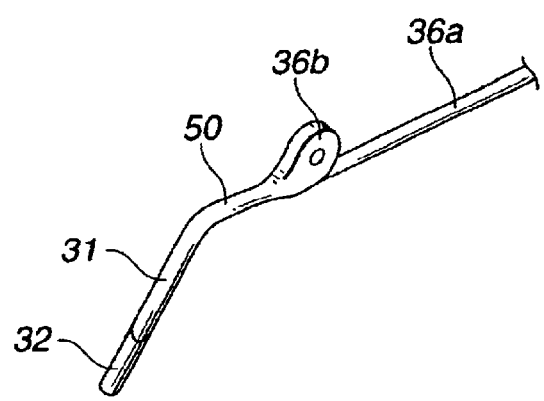
Figure 14C:
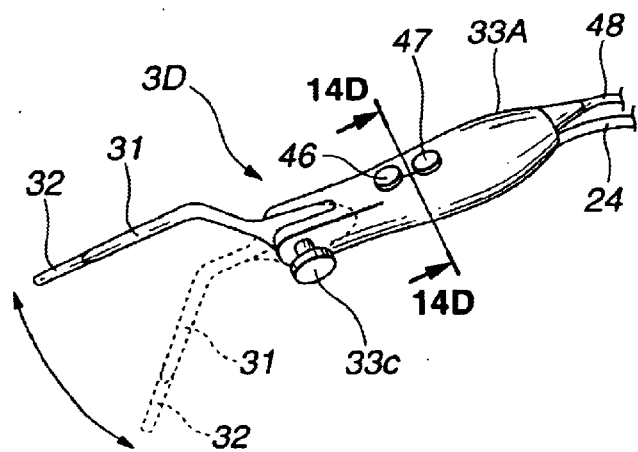

As shown in FIG. 14C, an observation body 3D consists of a handle member 33A shown in FIG. 14A and a probe passage member 50 freely detachably attached to the handle member 33A as shown in FIG. 14B. The probe passage member 50 is attached to the handle member 33A as an integral part of the handle member.

As shown in FIG. 14A, the handle member 33A has an adjustment knob 33c serving as an attachment mechanism for holding the probe passage member 50 so that the probe passage member can be detached freely and also serving as an angle adjustment mechanism to be described later. Moreover, the remote switches 46 and 47 are bared on the lateral surface of the handle member 33A. An electric cable 48 is extended from the proximal end of the handle member 33A. Signal lines extended from the remote switches 46 and 47 are contained in the electric cable 48.

On the other hand, as shown in FIG. 14B, the probe passage member 50 consists of the straight pipe 31, the distal cap 32, and a base placement portion 36a having an attachment 36b.

The adjustment knob 33c is tightened with the attachment 36b located at a predetermined position in the handle member 33A. Consequently, the direction of extension of the straight pipe 31 extending from the handle member 33A can be changed to a direction indicated with a solid line in FIG. 14C or a direction indicated with a dashed line therein. In other words, an angle at which the longitudinal axis of the handle member 33A and the longitudinal axis of the straight pipe 31 meets can be set to an operator's desired value.

Figure 14D:
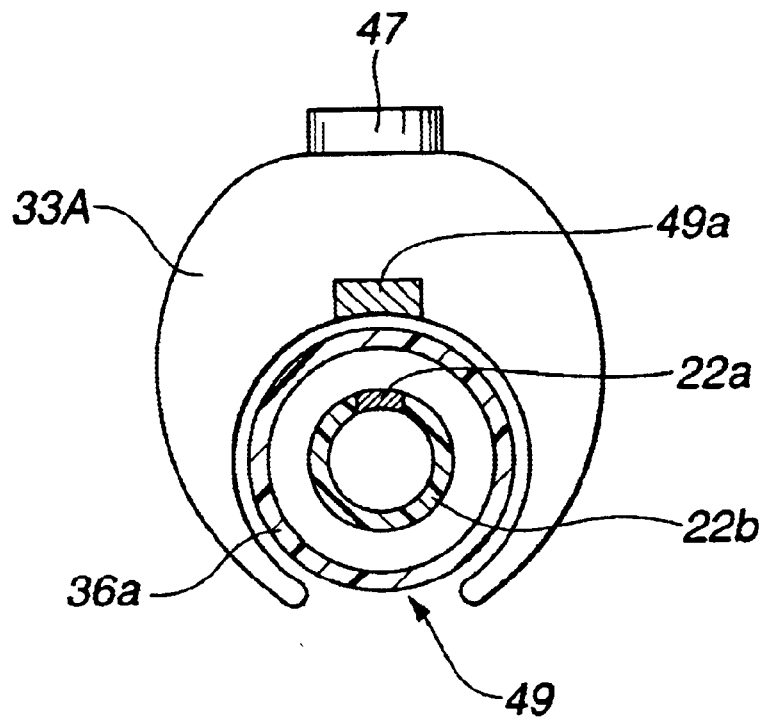
Figure 14E:
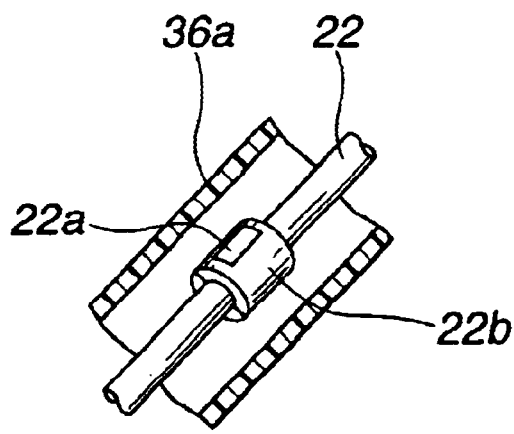

As shown in FIG. 14D, the handle member 33A has a placement concave part 49 in which the base placement portion 36 is fitted. A Hall-effect device 49a for sensing magnetic field strength is located at a predetermined position in the wall of the placement concave part 49. A sensing member 22b having a magnet 22a to be sensed by the Hall-effect device 49a is, as shown in FIG. 14E, located at a predetermined position in the flexible shaft 22 passed through the base placement portion 36a.

Consequently, the Hall-effect device 49a senses the magnet 22a included in the sensing member 22b mounted in the flexible shaft 22. As described in conjunction with FIG. 8C, the orientation of the handle member 33A is corrected so that the orientation of the magnet 22a sensed by the Hall-effect device 49a will remain constant (lie above in the drawings) all the time. An ultrasonic image is thus displayed on the screen. This helps an operator view the ultrasonic image while grasping the positional relationship between components of the handle member 33A and the positional relationship between things depicted in an ultrasonic image.

Figure 15:
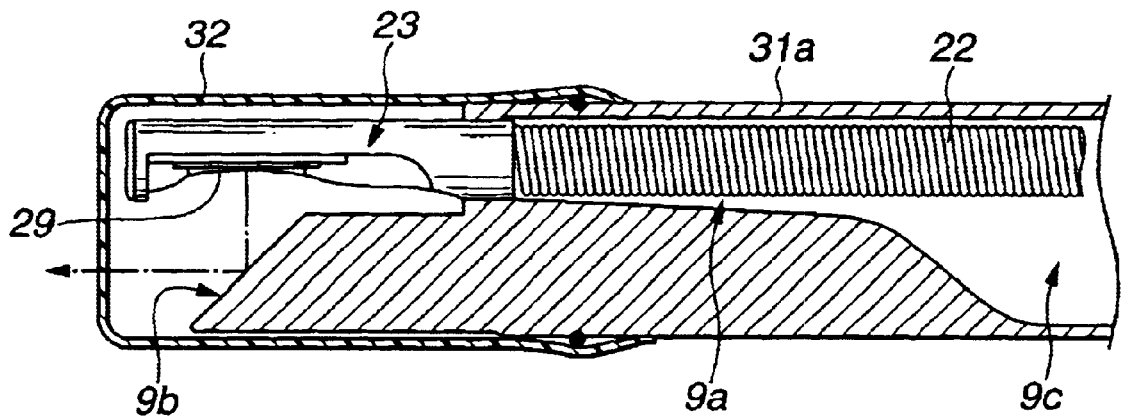
FIG. 15 to FIG. 17 are concerned with the fourth embodiment of the present invention.
Figure 16:
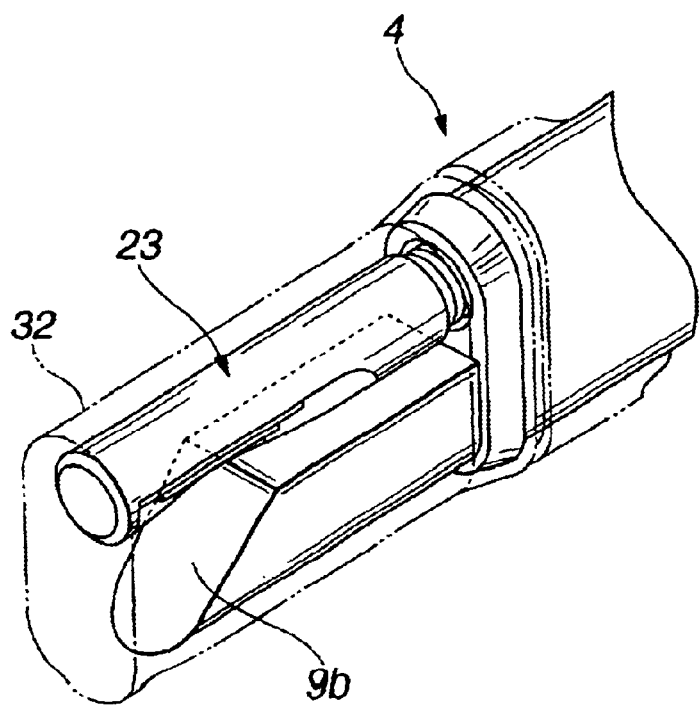
Figure 17:
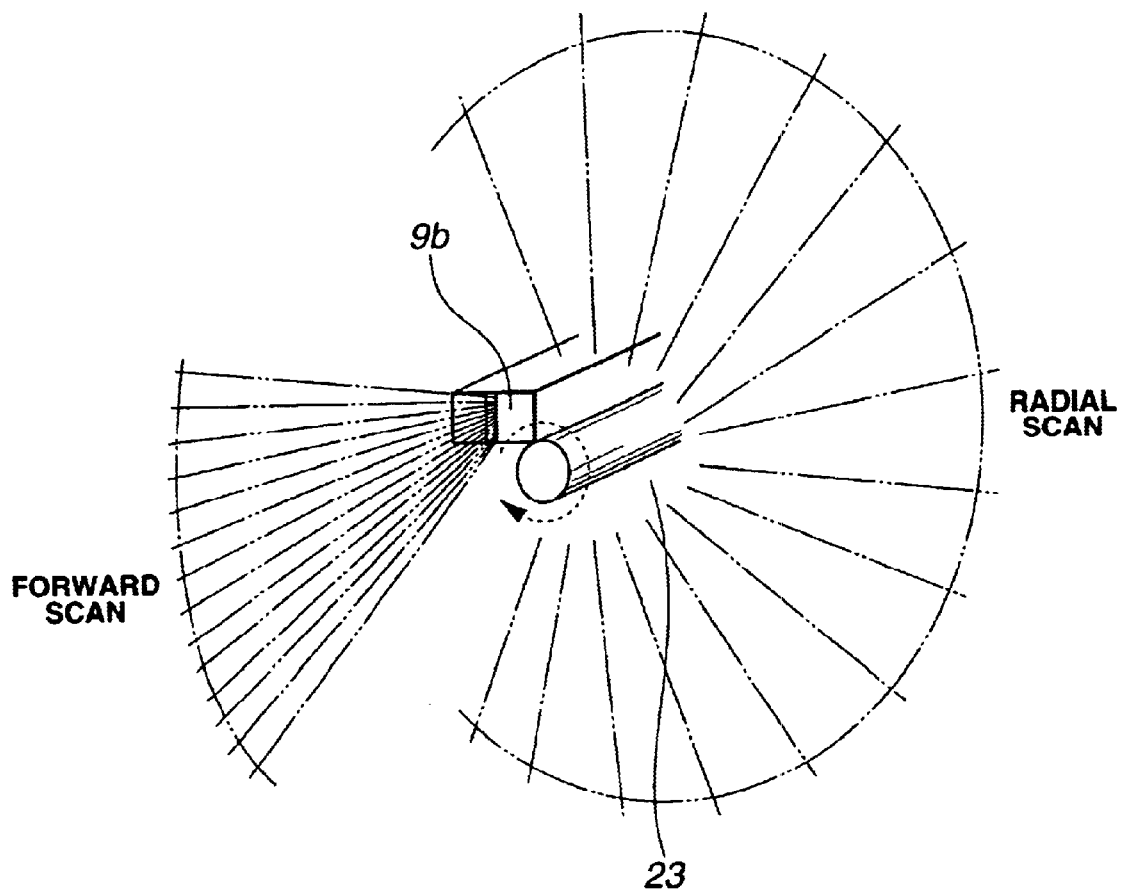

Referring to FIG. 15 to FIG. 17, the fourth embodiment of the present invention will be described below.

According to the first to third embodiments, the direction of scanning performed by the ultrasonic transducer 29 included in the microscopic probe 4 is orthogonal to the direction of insertion of the microscopic probe 4, and includes all directions within 360°. Thus, the microscopic probe produces a radial image. In contrast, according to the present embodiment, a microscopic probe is designed to produce both an image representing an area in a region located in a forward direction of insertion and a radial image.

As shown in FIG. 15 and FIG. 16, according to the present embodiment, a mirror-inclusive pipe 31a having, for example, a metallic ultrasound reflecting mirror included therein as a distal projection is substituted for the straight pipe 31 to which the distal cap 32 is fixed.

As shown in FIG. 15, the mirror-inclusive pipe 31a consists of a shaft placement hollow 9a, a reflecting mirror surface 9b, and a passage hole 9c. The flexible shaft 22 is passed through the shaft placement hollow 9a. The reflecting mirror surface 9b that is an distal surface of the projection formed in the shaft placement hollow 9a is inclined substantially 45° and opposed to the ultrasonic transducer 29. The transducer assembly 23 of the ultrasonic probe body 2 is passed through the passage hole 9c that serves as an escape recess intended to reduce the weight of the pipe 31a.

As shown in FIG. 15 and FIG. 16, the transducer assembly 23 is passed through the passage hole 9c and shaft placement hollow 9a, and routed to a predetermined position. Consequently, the reflecting mirror surface 9b is opposed to the ultrasonic transducer 29 of the transducer assembly 23.

When the rotating ultrasonic transducer 29 radiates ultrasonic waves in all directions within 360° as shown in FIG. 17, part of the radiated ultrasonic waves is reflected from the reflecting mirror surface 9b and propagated forwards.

In other words, according to the present embodiment, the ultrasonic transducer 29 included in the transducer assembly 23 radiates ultrasonic waves in all directions within 360°. Ultrasonic waves reflected from the reflecting mirror surface 9b are used to scan an area in a region located forwards. Ultrasonic waves not reflected from the reflecting mirror surface 9b but radiated in radial directions are used to scan areas in the region located in the radial directions. This results in both a forward image and a radial image.

Since the distal projection is included to provide the reflecting mirror surface 9b, part of the radial image is missing.

As mentioned above, the mirror-inclusive pipe has the reflecting mirror surface, which is inclined substantially 45° and opposed to the ultrasonic transducer, formed in the distal part thereof. The ultrasonic transducer radiates ultrasonic waves in all directions within 360°. Both a forward image produced with ultrasonic waves reflected from the reflecting mirror surface and a radial image produced with ultrasonic waves radiated in radial directions can be produced to facilitate observation of a lesion and treatment thereof.

Figure 18:
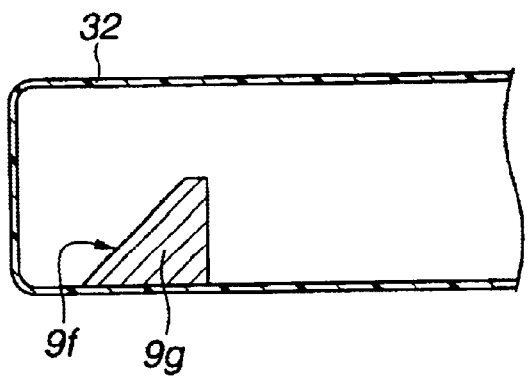
FIG. 18 is an explanatory diagram showing another example of the structure of a distal cap.

As shown in FIG. 18, an ultrasound reflecting mirror member 9g may be substituted for the reflecting mirror surface of the projection. The ultrasound reflecting mirror member 9g serves as an ultrasonic reflecting mirror having a reflecting mirror surface 9f inclined substantially 45°, and is formed in the distal part of the distal cap 32.

Figure 19:
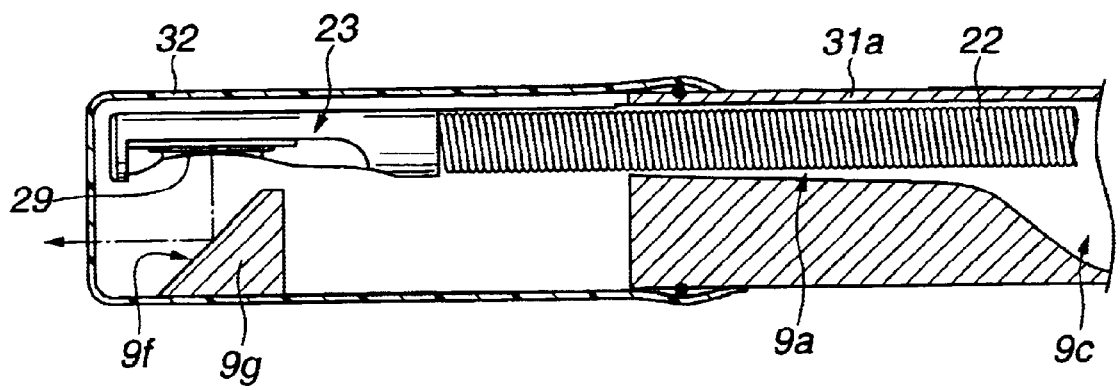
FIG. 19 is an explanatory diagram showing the position of the probe for producing a forward image and a radial image.

When the transducer assembly 23 is, as shown in FIG. 19, placed at a predetermined position in the distal part of the distal cap 32, the ultrasonic transducer 29 is opposed to the reflecting mirror surface 9f of the ultrasound reflecting mirror member 9g. This results in, as mentioned above, both a forward image produced with ultrasonic waves reflected from the reflecting mirror surface 9f and a radial image produced with ultrasonic waves radiated in radial directions.

Figure 20:
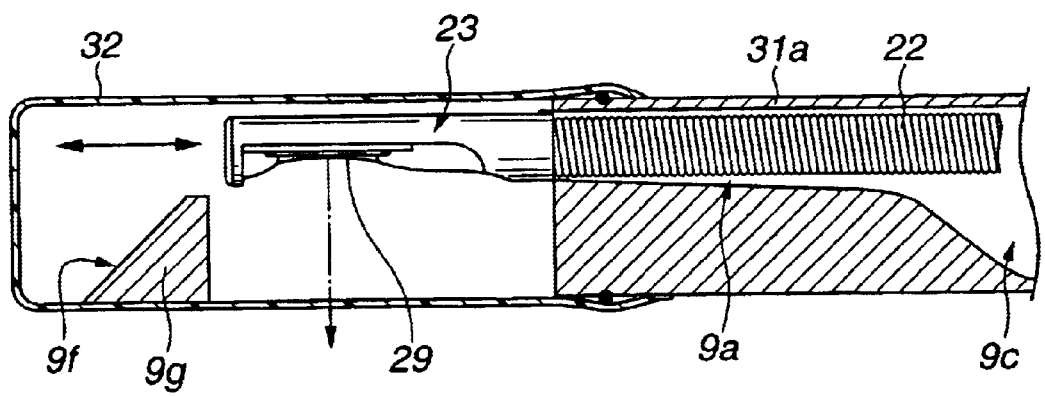
FIG. 20 is an explanatory diagram showing the position of the probe for producing a radial image that represents the whole range of 360°.

The ultrasonic transducer 29 may be, as shown in FIG. 20, placed at a predetermined position in the proximal part of the distal cap 32. At this position, the ultrasonic transducer 29 is not opposed to the reflecting mirror surface 9d. This results in a perfectly radial image representing areas in a region located in all directions within 360°.

As mentioned above, an operator advances or withdraws the ultrasonic transducer in the direction of insertion so as to set the ultrasonic transducer at a proper position. Consequently, both a forward image and a radial image are produced to facilitate observation of a lesion and treatment thereof. Otherwise, a radial image representing areas in a region located in all directions within 360° can be produced in order to selectively observe and treat a lesion.

Figure 21:
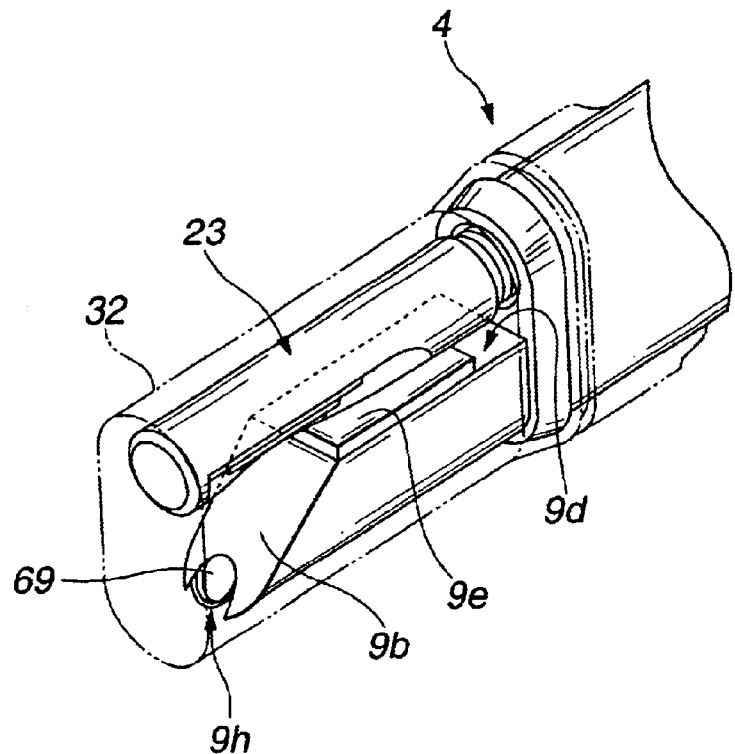
FIG. 21 is an explanatory diagram showing another example of the structure of an ultrasonic probe for microscopic operations.

As shown in FIG. 21, a groove 9h may be formed to open as part of the reflecting mirror surface 9d. In this case, an observation optical system 69 including an image guide fiber is fitted in the groove 9h. Consequently, an optical image of a region to be observed which is formed by the observation optical system 69 can be viewed in addition to an image formed in the field of view of the microscope. A position to which the distal cap is inserted can therefore be checked accurately.

Referring to FIG. 22 to FIG. 24C, an example of application of the fourth embodiment will be described below.

Figure 22:
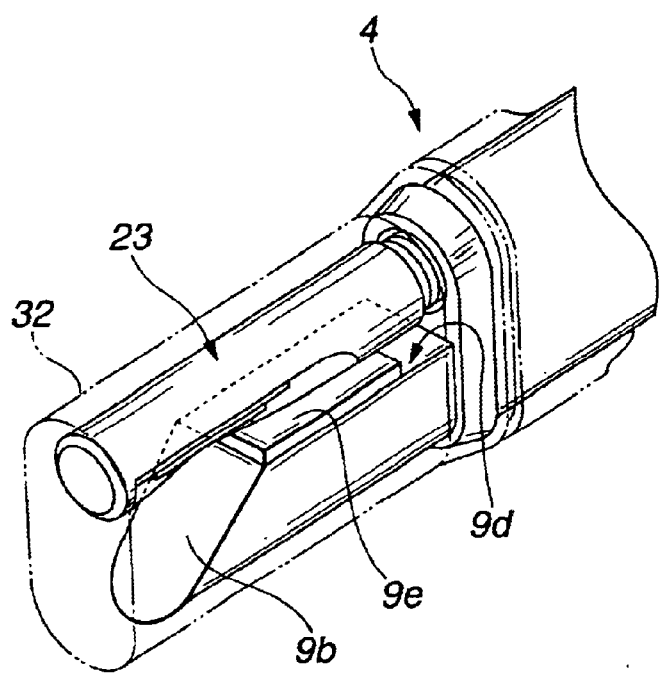

As shown in FIG. 22, a sound absorbing member 9e made of, for example, chloroprene rubber for absorbing ultrasonic waves is placed on a side surface 9d of the projection which communicates with the reflecting mirror surface 9b and extends near the ultrasonic transducer 29. Consequently, the sound absorbing member 9e absorbs ultrasonic waves emitted from the ultrasonic transducer 29. An artifact produced with ultrasonic waves reflected from the side surface 9d and propagated to the ultrasonic transducer 29 can be minimized. An excellent ultrasonic image can therefore be produced.

Figure 24C:
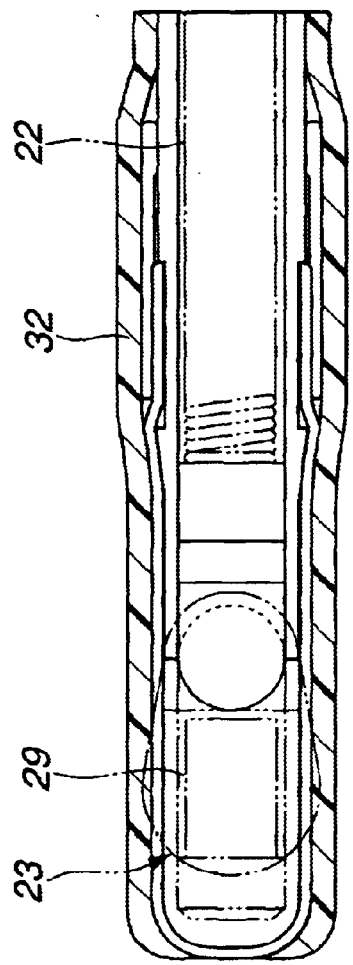
FIG. 24C is a 24C—24C sectional view of the reflecting mirror surface shown in FIG. 24B.
Figure 24B:
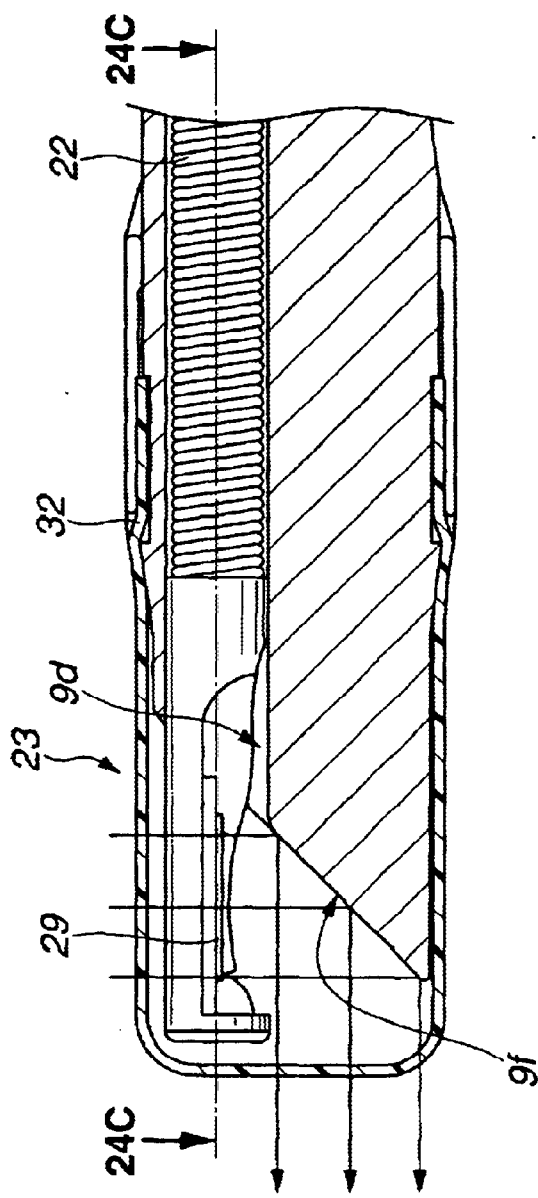
FIG. 24B is a side view of the reflecting mirror surface.
Figure 24A:
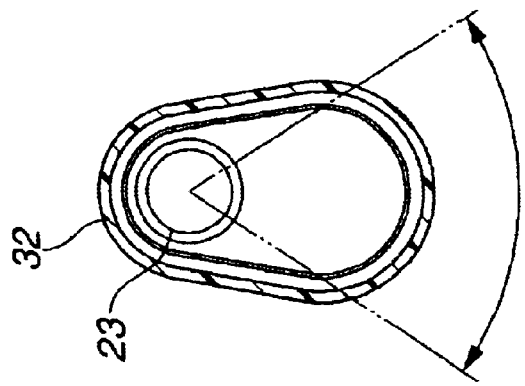

As shown in FIG. 24A, FIG. 24B, and FIG. 24C, the reflecting mirror surface 9f is opposed to the whole radiating surface of the ultrasonic transducer 29. This is intended to prevent ultrasonic waves emitted from the ultrasonic transducer 29 from falling on the ultrasonic transducer 29 again after being reflected from the side surface 9d. Consequently, the side surface 9d is not opposed to the ultrasonic transducer 29. Nevertheless, an excellent ultrasonic image can be produced with an artifact minimized. Moreover, the reflecting mirror surface 9f is formed to have the width thereof made wider towards the lower side thereof. The angle of view determining the size of a forward plane to be scanned becomes wider.

Since the sound absorbing member 9e is placed on the side surface 9d of the projection which communicates with the reflecting surface 9f and extends near the ultrasonic transducer 29, ultrasonic waves reflected irregularly are absorbed. Eventually, an excellent ultrasonic image can be produced with an artifact minimized effectively.

Figure 23:
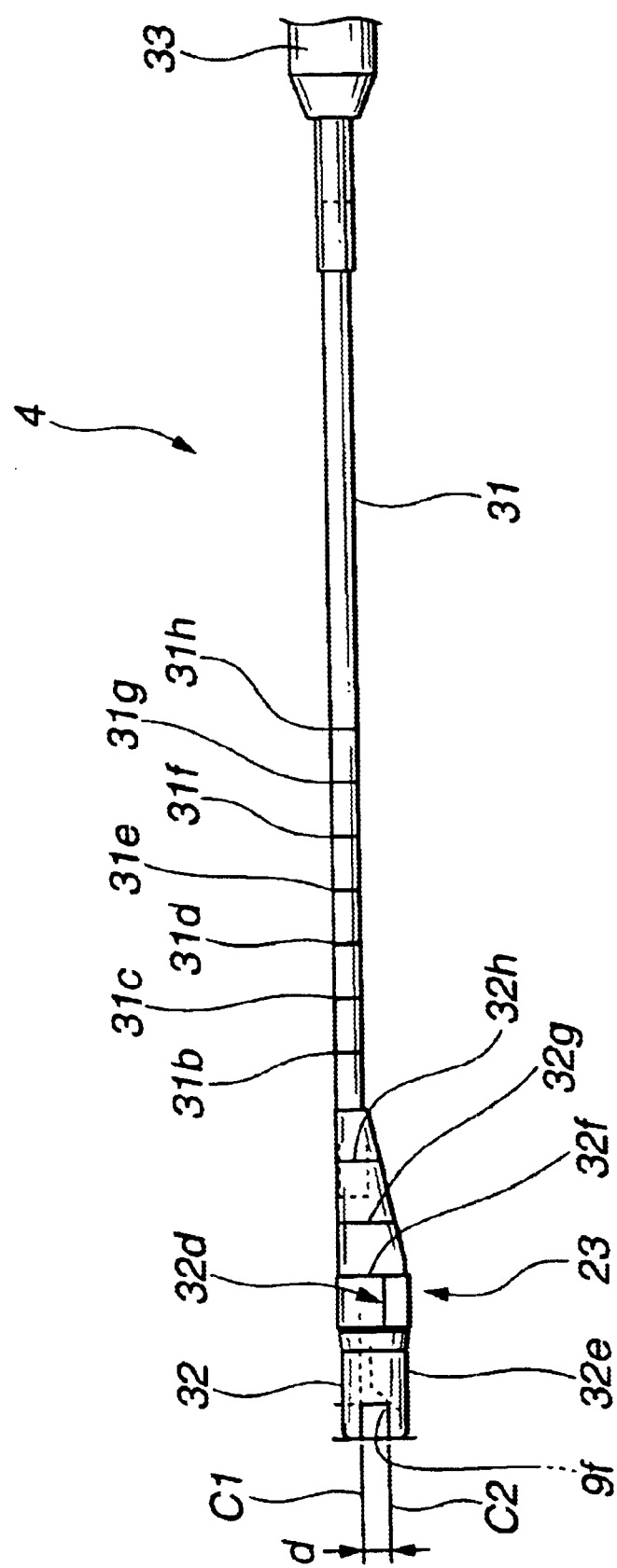

In the aforesaid embodiment, the reflecting mirror surface 9f shaped to have the width thereof made wider towards the lower side thereof is formed to be opposed to the whole radiating surface of the ultrasonic transducer 29. Consequently, as shown in FIG. 23, the centerline (axis) C1 of the flexible shaft 22 and the centerline (axis) C2 of a scanned plane located ahead of the reflecting mirror surface 9f are separated from each other by a distance d. For this reason, a forward scanned plane index 32d is marked at a predetermined position on the surface of the distal cap 32 enclosing the transducer assembly 23 so that the center point on the forward scanned plane can be identified at sight. Consequently, the centerline C2 passing through the forward scanned plane located ahead of the reflecting mirror surface 9f can be aligned with the center of an intended area in a lumen. The forward scanned plane index 32d is marked using, for example, a laser.

Furthermore, depth indices 32e, 32f, 32g, and 32h with which a user learns a length of insertion, by which the microscopic probe has been inserted, at sight are marked on the distal cap 32 using a laser. The depth indices 32e, 32f, 32g, and 32h enable an operator to grasp the length of insertion instantaneously while looking through the microscope.

Depth indices 31b, 31c, 31d, etc. may also be marked on the outer surface of the straight pipe 31 included in the microscopic probe 4. This makes it possible to grasp a length of insertion, by which the microscopic probe 4 has been inserted, instantaneously while looking through the microscope.

Moreover, when the outer surface of the straight pipe 31 is made of a metal, the metallic outer surface is satin-finished. This is intended to prevent the surface of the pipe from glittering unnecessarily during use of the microscopic probe.

Referring to FIG. 25 to FIG. 31B, the fifth embodiment of the present invention will be described below.

Figure 25:
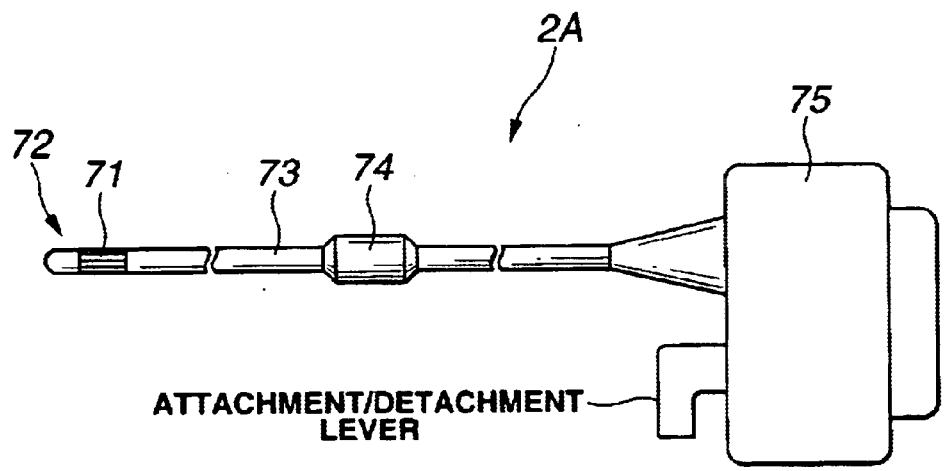

According to the aforesaid first to fourth embodiments, the transducer assembly 23 included in the microscopic probe 4 has the ultrasonic transducer 29 incorporated in the housing 28 thereof. The housing 28 is mechanically rotated using the flexible shaft 22 that conveys driving torque of the motor included in the probe drive unit 10. According to the present embodiment, a plurality of transducer elements is, as shown in FIG. 25, arranged circumferentially regularly as the distal part of an ultrasonic probe body in order to construct a transducer assembly 62. Thus, the present embodiment employs an electronic radial scanning type ultrasonic probe body 2A in which the transducer elements 71 are electrically driven to rotate for scanning.

The ultrasonic probe body 2A consists mainly of a transducer assembly 72, a soft elongated signal cable 73, a locking base 74, and a connector 75. The transducer assembly 72 has the plurality of transducer elements 71 arranged, for example, circumferentially regularly. The soft elongated signal cable 73 accommodates signal lines (not shown) extended from the transducer elements 71 constituting the transducer assembly 72. The locking base 74 is located at the middle of the signal cable 73, and has a body locking screw abutted thereon similarly to the stepped base 25. The connector 75 is located at the proximal end of the signal cable 73, and coupled to an ultrasound observation unit so that it can be uncoupled freely. The ultrasound observation unit includes an ultrasound transmission/reception circuit for driving the transducer elements 71 and transmitting or receiving ultrasonic waves. The connector 75 has an attachment/detachment lever.

Figure 26A:
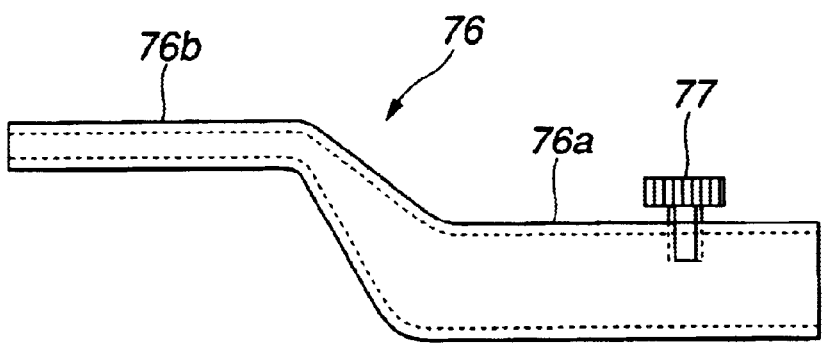
FIG. 26A and FIG. 26B are explanatory diagrams showing an observation body suitable for the ultrasonic probe body.
Figure 26B:
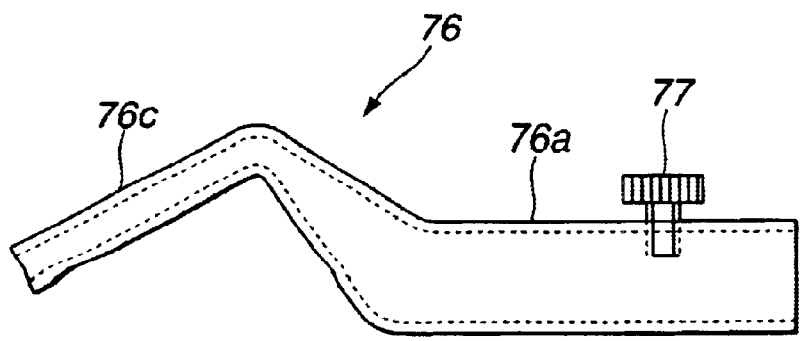

On the other hand, an observation body 76 through which the ultrasonic probe body 2A is passed has, as shown in FIG. 26A, an uneven linkage portion 76a and a pipe portion 76b joined as a united body. The pipe portion 76b has a distal end thereof left open, and is shaped straight and parallel to the centerline (axis) of the uneven linkage portion 76a. Otherwise, a pipe portion 76c that is bent with respect to the centerline (axis) of the uneven linkage portion 76a, and the uneven linkage portion 76a are joined to construct the observation body 2A. A body locking screw 77 is located at a predetermined position of the uneven linkage portion 76a.

Figure 27:
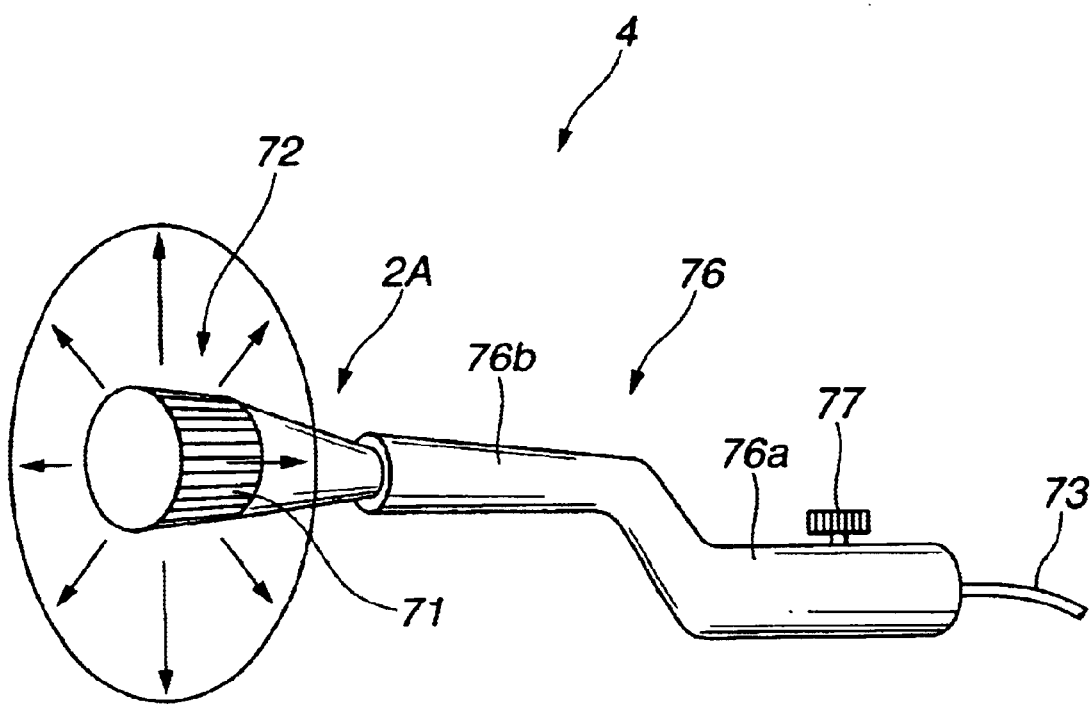

As shown in FIG. 27, the ultrasonic probe body 2A is passed through the observation body 76, and the body locking screw 77 is tightened to lock the locking base 74. Consequently, the ultrasonic probe body 2A and observation body 76 are joined with the transducer assembly 72 jutted out of the opening of the pipe portion 76b of the observation body 76, thus constructing the electronic radial scanning type microscopic probe 4.

As mentioned above, the ultrasonic probe body having the plurality of transducer elements arranged as the distal part thereof is placed at the predetermined position in the observation body having the distal end thereof left open, thus constructing the electronic microscopic probe. Consequently, the same operations and advantages as those provided by the aforesaid embodiments can be provided.

Figure 28:
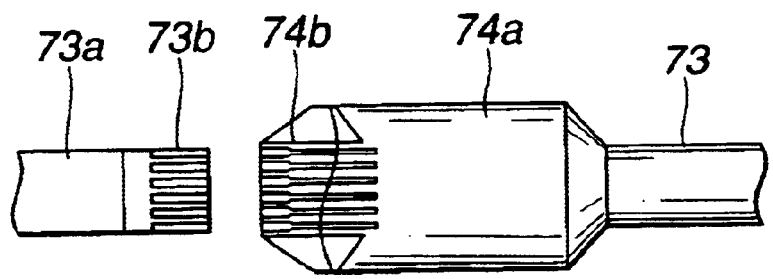

As shown in FIG. 28, the locking base 74 may be formed as a locking base-cum-cable connector 74a having an electrode pattern 74b drawn thereon. A transducer assembly-inclusive signal cable 73a has an electrode pattern 73b drawn on a proximal part thereof is electrically and mechanically attached to the distal part of the locking base 74 having the electrode pattern 74b drawn thereon. Only the transducer assembly-inclusive signal cable 73a having the transducer assembly 72 that does not resist the conditions for autoclaving, that is, high temperature and high humidity is designed to be disposable. This leads to an inexpensive ultrasonic probe body.

Figure 29A:
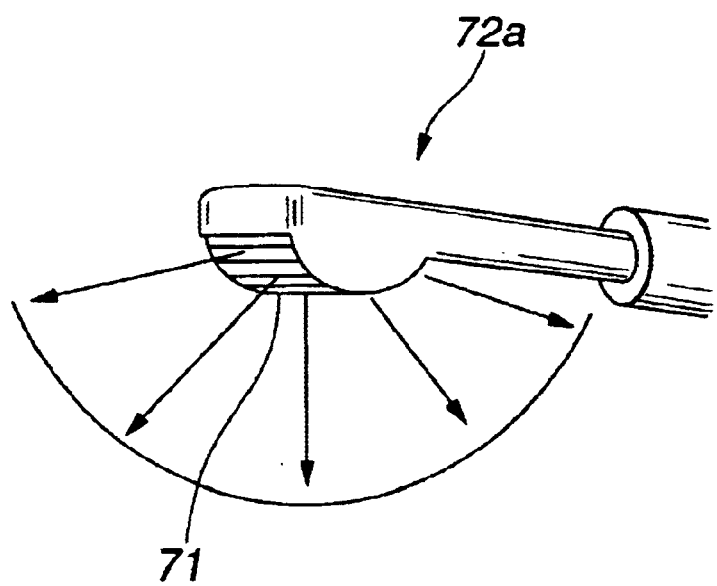
Figure 29B:
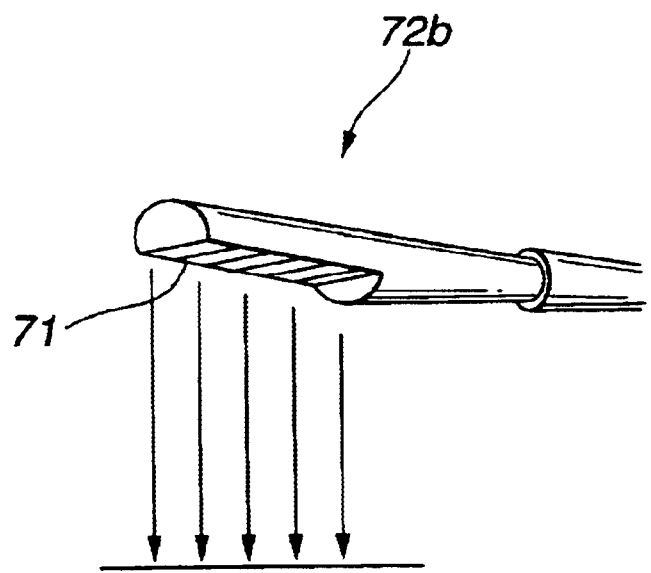

Moreover, the electronic transducer assembly 72 is not limited to the radial scanning technique. For example, as shown in FIG. 29A, the plurality of transducer elements 71 may be arranged radially in order to thus construct a convex scanning type transducer assembly 72a that scans a radial ultrasonically observable range. Otherwise, as shown in FIG. 29B, the plurality of transducer elements 71 may be lined in the direction of insertion in order to thus construct a linear scanning type transducer assembly 72b that scans an ultrasonically observable range extended in the direction of insertion. In this case, scan heads that are the transducer assemblies can be switched according to a purpose of use. This leads to improved efficiency in observation.

Figure 30A:
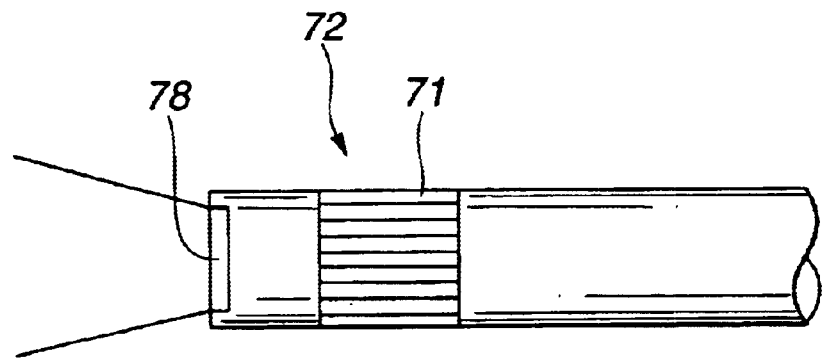
FIG. 30A to FIG. 30C are explanatory diagram showing another examples of a structure included in an electronic ultrasonic probe for microscopic operations.
Figure 30B:
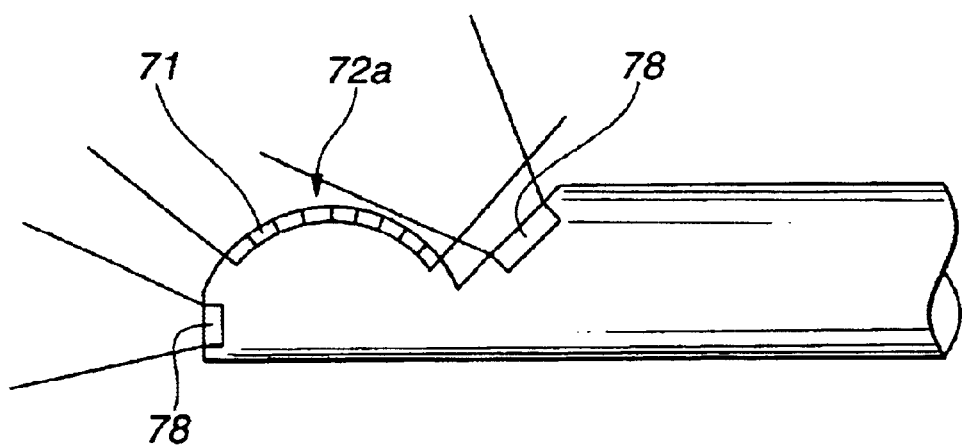
Figure 30C:
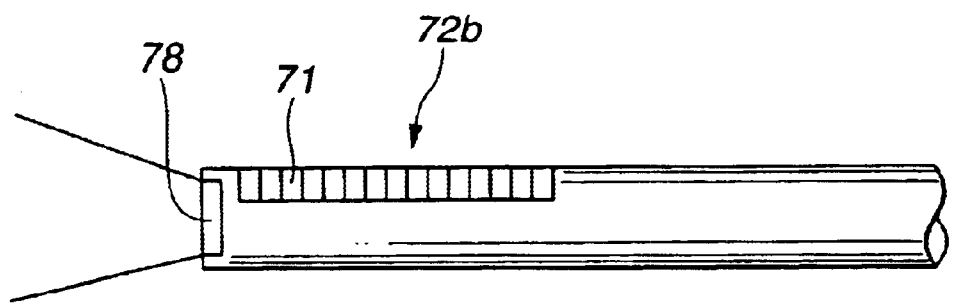

Furthermore, as shown in FIG. 30A, an observation optical system 78 including an image guide fiber may be included in the radial scanning type transducer assembly 72. As shown in FIG. 30B, the observation optical system 78 may be included in the convex scanning type transducer assembly 72a. Moreover, as shown in FIG. 30C, the observation optical system 78 may be included in the linear scanning type transducer assembly 72b. In this case, in addition to an image formed in the field of view of the microscope, an optical image of a region to be observed formed by the observation optical system 78 can be viewed for checking a position to which the microscopic probe is inserted.

Figure 31A:
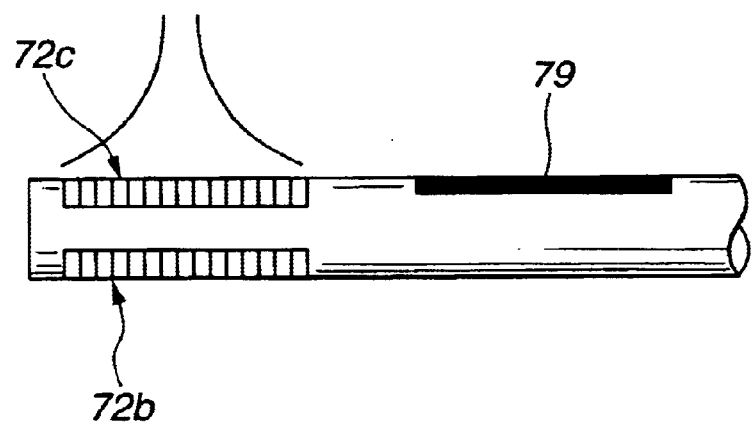
FIG. 31A and FIG. 31B are explanatory diagrams showing another example of a structure included in the electronic ultrasonic probe for microscopic operations.
Figure 31B:
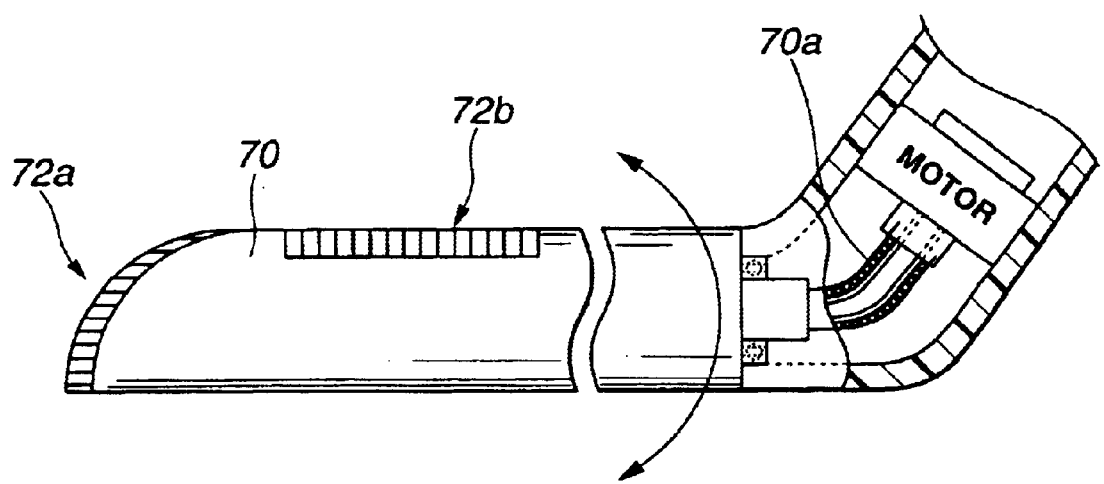

Moreover, in addition to the linear scanning type transducer assembly 72b having the transducer elements 71 lined, a therapeutic transducer assembly 72c having therapeutic transducer elements lined may be included as shown in FIG. 31A. The convex scanning type transducer assembly 72a and linear scanning type transducer assembly 72b may be included in a distal member 70 as shown in FIG. 31B. The distal member 70 may be rotated with driving torque exerted by a motor and conveyed over a flexible shaft 70a, whereby a three-dimensional ultrasonic view image may be produced. Incidentally, a mark 79 allows a user to visually identify the direction of an extension of the therapeutic transducer assembly 72c. Namely, the mark 79 informs a user of the direction of the therapeutic transducer assembly 72c.

Figure 32:
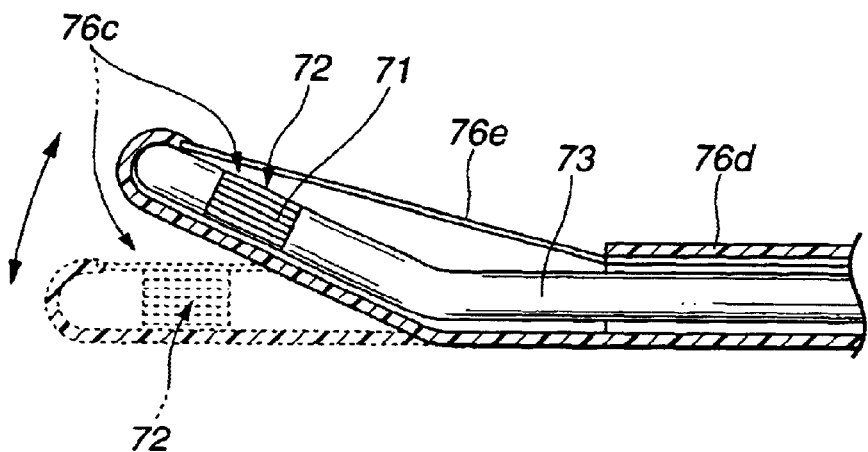

As shown in FIG. 32, a flexible bending sheath member 76d that has a notch 76c in which the transducer assembly 72 is fitted may be formed as the distal part of the pipe portion 76b. Besides, an angling wire 76e is stretched over the notch 76c. The angling wire 76e is hauled in line with the shape of a lumen of a region having a lesion, whereby the bending sheath member 76d is bend from a straight state indicated with dashed lines to a bent state indicated with solid lines. Thus, ultrasonic images representing areas in the region located in various directions can be produced. Moreover, the pipe portion 76b having the notch 76c may be replaced with the bending member 64. In this case, the bending member 64 can be bent in a desired direction by manipulating the angling wires 68. Consequently, ultrasonic images representing areas in a region located in various directions can be produced. The other operations and advantages are identical to those of the aforesaid embodiments.

As described in conjunction with FIG. 23, the depth indices 32e, etc. and 32h, and 31b, etc. and 31h may be marked on the distal cap 32 and straight pipe 31. This helps a user instantaneously grasp a length of insertion by which the microscopic probe has been inserted while looking through the microscope. Even in this case, if blood or the like is mixed in physiological saline injected into a lumen of a region to be observed during ultrasonic examination, it becomes hard to identify the distal end of the microscopic probe through the microscope. This may hinder observation.

Figure 33:
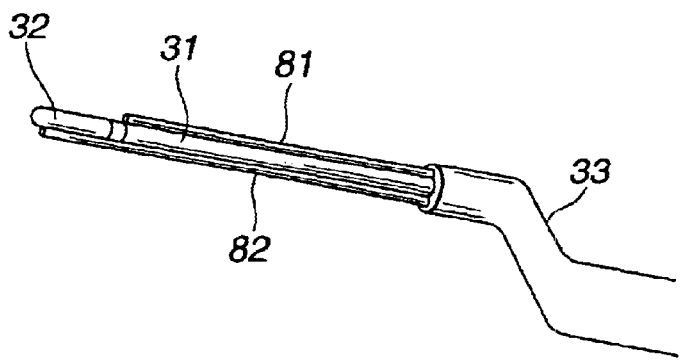

For preventing the above incident, as shown FIG. 33, a fluid supply channel 81 and a suction channel 82 are laid in contact with the straight pipe 31, bellows pipe 54, or pipe portion 76b included in the observation body. Physiological saline is supplied through the fluid supply channel 81. Physiological saline mixed with blood is sucked through the suction channel 82. The distal end of one of the channels, for example, the suction channel 82 is located near the distal end of the distal cap 32.

Consequently, if blood or the like is mixed in physiological saline, it becomes hard to form an image in the field of view of the microscope. In this case, the physiological saline mixed with blood is sucked through the suction channel 82 and discharged. At the same time, physiological saline is supplied through the fluid supply channel 81. In other words, physiological saline is circulated in order to restore the transparency characteristic of physiological saline. Eventually, a view image can be observed through the microscope.

Moreover, the distal end of the suction channel 82 is located near the distal end of the distal cap 32. Consequently, the distal end of the suction channel 82 is located ahead of the radiating surface of the ultrasonic transducer. An ultrasonic image of the suction channel 82 is therefore depicted in an ultrasonic image of an intended region. this helps orient the microscopic probe. Incidentally, the foregoing structure can be adapted irrespective of whether the transducer assembly is mechanically or electrically driven.

Moreover, in the aforesaid embodiments, physiological saline is injected into the lumen of a region to be observed in order to perform ultrasonic examination. The transducer assembly may be enclosed in a balloon that can be freely dilated or shrunken. Physiological saline is then supplied to the balloon, whereby the balloon is dilated. This causes the surface of the balloon to come into close contact with the wall of the lumen. The region is then observed ultrasonically.

Figure 34:
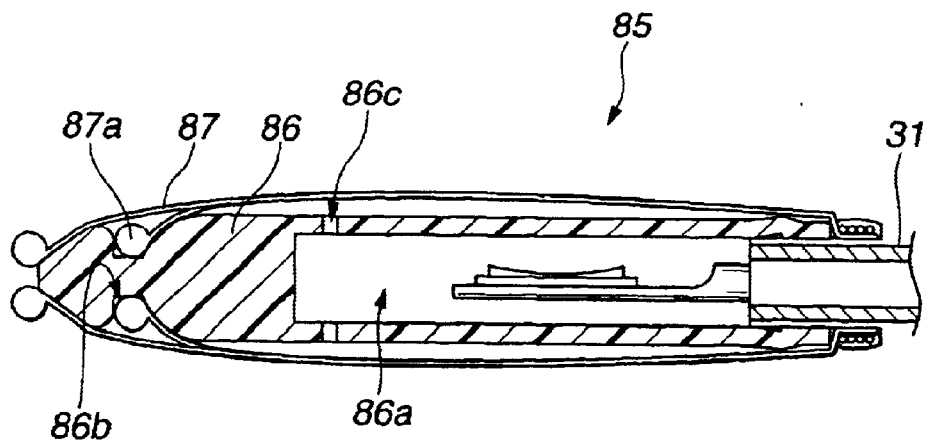

A distal cap 86 has a space 86a and a distal groove 86b. The transducer assembly 23 is placed in the space 86a. The distal groove 86b has a predetermined shape and depth and serves as an engaging/locking portion in which part of a balloon 87 is locked so that it can be unlocked freely. Thus, a balloon assembly 85 is constructed as shown in FIG. 34. The balloon 87 can be freely dilated or shrunken, and can substantially entirely shield the periphery of the distal cap 86. The balloon 87 is realized with a balloon member made of latex, Teflon rubber, or any other material that can transmit ultrasonic waves and can be freely stretched or contracted.

The balloon 87 has the proximal end thereof fixed to the periphery of the straight pipe 81 as an integral part of the straight pipe 31 through bobbin winding bonding. The distal part of the balloon 87 encloses the periphery of the distal cap 86 while partly being locked in the distal groove 86b with a balloon O ring 87a. The balloon O ring 87a is fitted in the distal groove 86b from the distal end of the distal cap 86 in order to seal a clearance around the periphery of the distal cap in a watertight manner. The balloon O ring 87a can be removed freely.

Moreover, one or a plurality of side holes 86c that links the space 86a and the outside of the distal cap 86 is bored in the lateral surface of the distal part of the distal cap 86. Through the side holes 86c, an ultrasound propagating medium such as physiological saline is poured into the balloon 87.

Figure 35A:
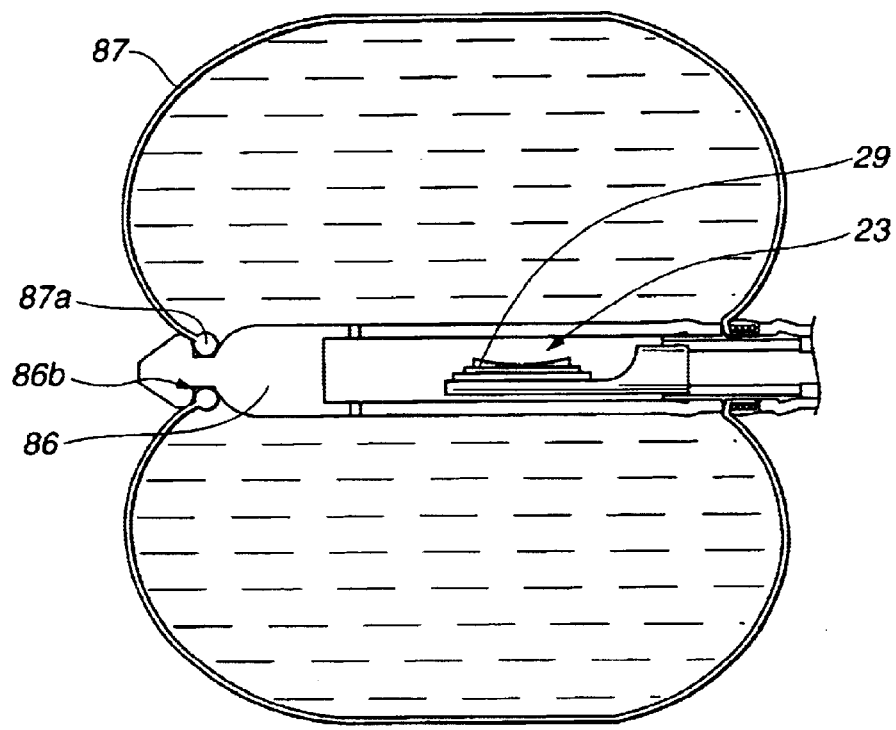
FIG. 35A and FIG. 35B are explanatory diagrams concerning the operation of the balloon.

As shown in FIG. 35A, when the ultrasound propagating medium is injected, the ultrasound propagating medium once reserved in the space 87a passes through the side holes 86c and flows into the clearance between the balloon 87 and the periphery of the distal cap 86. At this time, since the balloon O ring 87a is fitted in the distal groove 86b, the balloon 87 is dilated due to the ultrasound propagating medium flowing through the side holes 86c. The balloon 87 held dilated is brought into close contact with an intended region to be observed, and the ultrasonic transducer 29 is rotated. Thus, an ultrasonic view image of the intended region can be viewed.

Figure 35B:
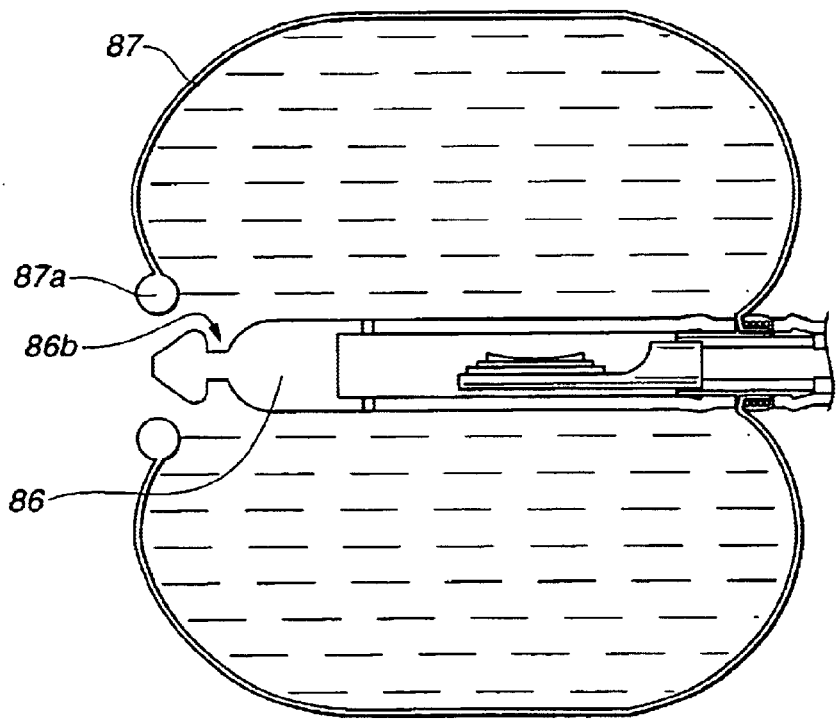

If too much ultrasound propagating medium is injected to the balloon 87, the internal pressure of the balloon 87 rises. This causes force to work on the balloon O ring 87a to press the balloon O ring 87a towards the distal end of the distal cap in the longitudinal direction. Therefore, before the balloon 87 is dilated so largely as to be ruptured, the balloon O ring 87a is, as shown in FIG. 35B, pushed out of the distal groove 86 towards the distal end of the distal cap and comes off. This causes the ultrasound propagating medium fed into the balloon 87 to flow out through the opening of the balloon 87. At this time, since the proximal end of the balloon is fixed to the periphery of the straight pipe 31 as an integral part of the straight pipe 31 through bobbin winding bonding, the balloon 87 will therefore not fall. Incidentally, the transducer assembly is shown to be of a mechanically driven type. Alternatively, the transducer assembly may be of an electronically driven type.

Figure 36:
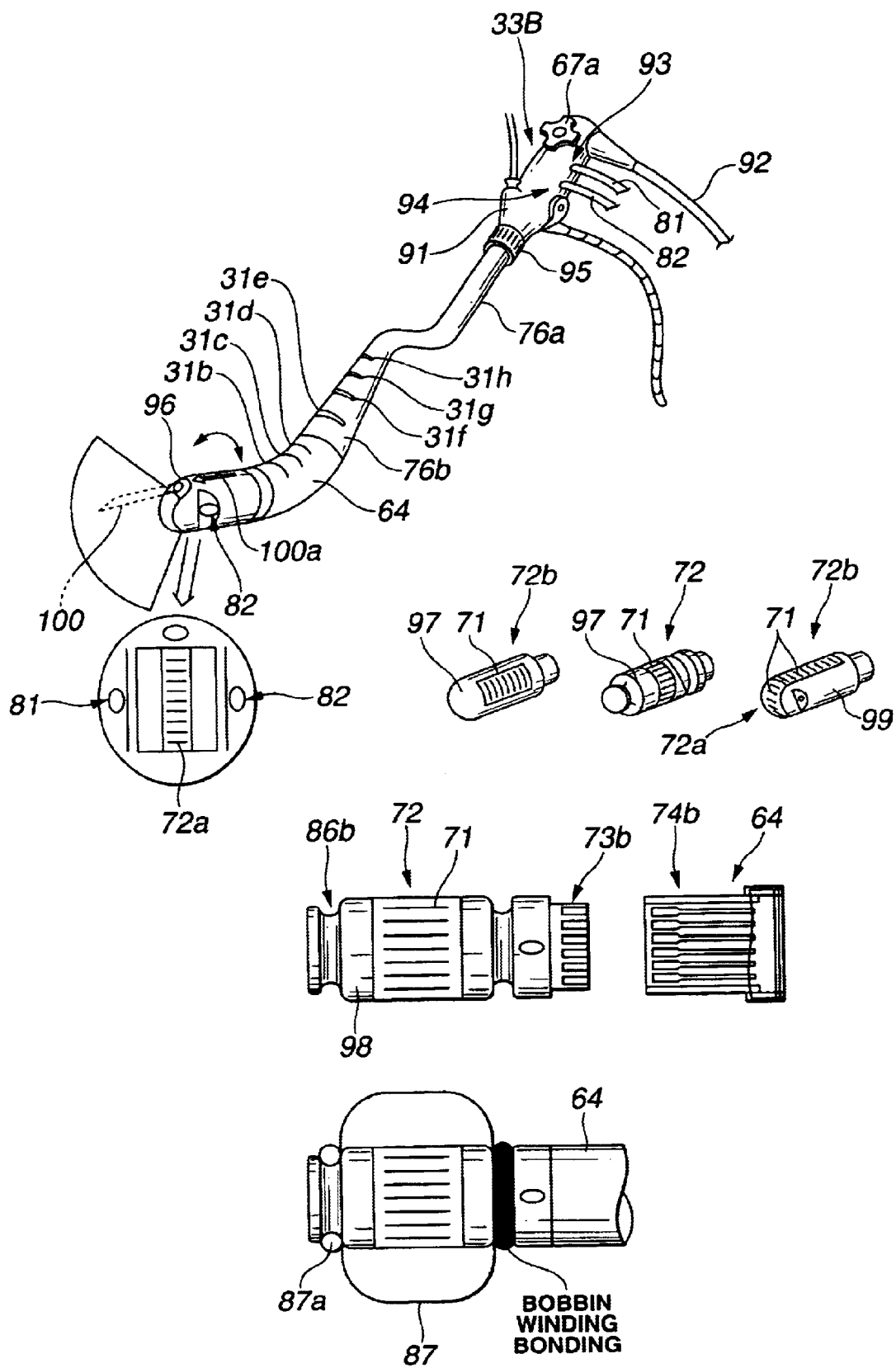
FIG. 36 is an explanatory diagram showing an example of the components of an electronic microscopic probe.

When an attempt is made to realize an electronic microscopic probe having the aforesaid constituent features, the microscopic probe is preferably constructed as shown in FIG. 36.

Specifically, a handle member 33B is configured to have a treatment appliance insertion port 91, an angling knob 67a, a universal cord 92, channel exits 93 and 94, and a fixture 95. The universal cord 92 accommodates signal lines and the flexible shaft. The fluid supply channel 81 and suction channel 82 are led out of the handle member through the channel exits 93 and 94. The fixture 95 is used to fix the proximal end of the uneven linkage portion 76a so that the uneven linkage portion 76a can be unfixed freely. At this time, the universal cord 92, the fluid supply channel 81, the suction channel 82, and a treatment appliance coming out of the treatment appliance insertion port 91 are laterally led out of the handle member in order to prevent them from hitting the microscope.

Thereafter, the bending member 64 is attached to the distal end of the pipe portion 76b. The indices 31b, 31c, 31d, etc. are marked on the outer surfaces of the bending member 64 and pipe portion 76b. Transducer assembly units 96, 97, 98, and 99 of various scanning types are made available so that they can be freely attached or detached to or from the distal end of the bending member 64. The transducer assembly units 96, 97, 98, and 99 include the convex scanning type transducer assembly 72a, the linear scanning type transducer assembly 72b, the radial scanning type transducer assembly 72, and a combination of the transducer assembly 72a and transducer assembly 72b respectively. At this time, the electrode patterns 73b and 74b are drawn on the transducer assemblies and the bending member respectively.

An opening through which a treatment appliance juts out may be bored in the transducer assembly units. In this case, a treatment appliance 100 inserted through the treatment appliance insertion port 91 can be led out of the transducer assembly unit as indicated with dashed lines. Moreover, the distal groove 86b in which the distal part of the balloon 87 is locked may be formed in the transducer assembly units. A mark 100a indicates a direction in which a treatment appliance should be introduced and also serves as a scanned plane index.

In the aforesaid embodiments, driving torque exerted by the motor included in the probe drive unit 10 is conveyed over the one elongated flexible shaft 22 in order to rotate the transducer assembly 23. For conveying the driving torque exerted by the motor included in the probe drive unit 10 to the transducer assembly 23 on a stable basis, the flexible shaft must have a somewhat large diameter. However, for passing the microscopic probe through a very thin lumen, the flexible shaft must be small in diameter. For this reason, there is a demand for a thin flexible shaft structured to be able to convey driving force stably.

Figure 37:
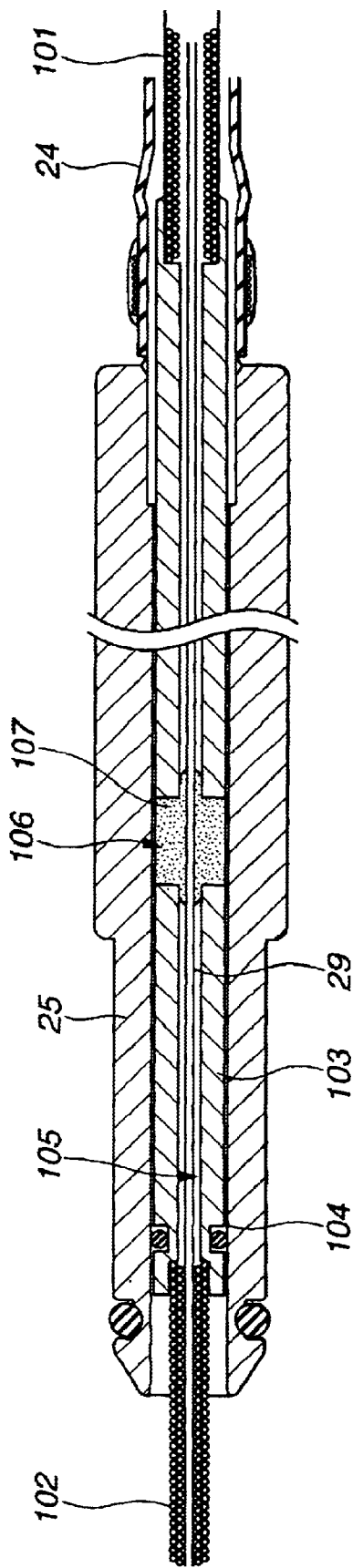
FIG. 37 shows an example of the structure of a flexible shaft.

As shown in FIG. 37, according to the present embodiment, a flexible shaft for conveying driving force consists mainly of a first flexible shaft 101 and a second flexible shaft 102.

Specifically, the first flexible shaft 101 having a large diameter and aiming to convey torque reliably is used to link the connector 21 and the proximal end of the stepped base 25. The second flexible shaft 102 having a small diameter in line with the dimensions of the observation body 3 through which the second flexible shaft is passed is used to link the distal end of the stepped base 24 and the proximal end of the housing 28. Within the stepped base 25, the first flexible shaft 101 and second flexible shaft 102 are joined as a united body using a pipe-shaped relay shaft 103.

Consequently, driving torque exerted by the motor that is not shown is conveyed to the housing 28 over the first flexible shaft 101, relay shaft 103, and second flexible shaft 102.

An O ring 104 is attached to the distal end of the relay shaft 103 in order to seal in a watertight manner the clearance between the wall of the base and the periphery of the relay shaft. A side hole 106 communicating with a hollow 105 is bored substantially at the middle of the relay shaft 103. An adhesive 87 is poured into the hollow 105 by way of the side hole 106, whereby the signal line 29 is secured. At the same time, the hollow 105 is divided into a distal part and a proximal part.

As mentioned above, the two flexible shafts having different diameters are joined as a united body using the relay shaft, thus realizing a flexible shaft for conveying torque. Consequently, torque of a desired level can be conveyed efficiently over the flexible shafts having desired diameters. Although the flexible shaft having a small diameter is employed, the transducer assembly can be rotated stably.

Moreover, the adhesive is poured into the hollow of the relay shaft in order to divide the hollow into the distal and proximal parts. Consequently, filth can be reliably prevented from entering a flexible shaft. This leads to improved cleaning efficiency.

A typical probe drive unit consists mainly of a motor, an encoder serving as a detecting means, a slip ring serving as a signal transmitting means, and a rotation control circuit. A flexible shaft is coupled to the motor. An ultrasonic transducer serving as an ultrasound transmission/reception unit is rotated by way of the flexible shaft. For detecting the position of the rotating ultrasonic transducer, the encoder is attached to the motor for driving and rotating the ultrasonic transducer. The encoder is corrected so that the position detected by the encoder will agree with the actual position of the scanning transducer. Thus, an ultrasonic image is produced.

However, the aforesaid microscopic probe includes a flexible shaft having a small diameter. It is therefore hard to stably convey driving torque exerted by the motor to the ultrasonic transducer. An ultrasonic image highly precisely representing a region is hard to produce.

Figure 38:
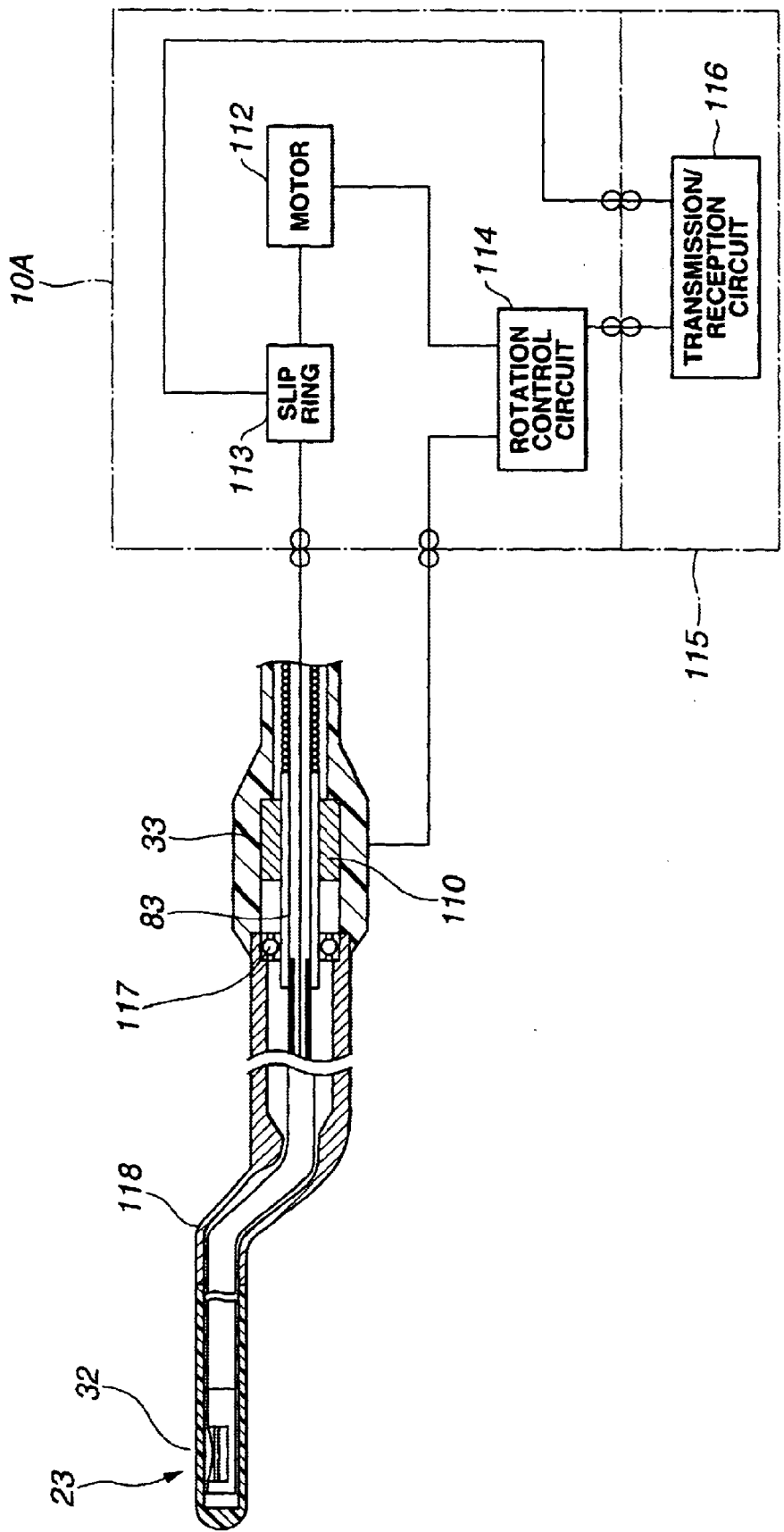
FIG. 38 is an explanatory diagram showing an example of a configuration for improving the performance of a mechanical ultrasonic probe for microscopic operations enabling observation.

According to the present embodiment, as shown in FIG. 38, a penetrating hollow-inclusive encoder 110 having a hollow through which the relay shaft 103 is passed is adopted and located at a predetermined position in the handle member 33. The encoder 110 optically or magnetically detects the position of the rotating transducer and outputs a position-of-rotating transducer signal to a rotation control circuit 114 to be described later over a signal cable 111.

A probe drive unit 10A employed in the present embodiment consists of a motor 112, a slip ring 113, and the rotation control circuit 114 but does not include an encoder. A transmission/reception circuit 116 included in an ultrasonic observation apparatus 115 is connected to the probe drive unit 10A.

Moreover, a bent pipe member 118 having a bearing 117, which bears the relay shaft 103 so that the relay shaft 103 can rotate freely, is freely detachably attached to the handle member 33.

As mentioned above, the penetrating hollow-inclusive encoder is included in the handle member. This results in the shortened distance between the ultrasonic transducer and the encoder. The position indicated with the position-of-rotating transducer signal output from the encoder agrees with the actual position of the transducer. Eventually, an ultrasonic image highly precisely representing a region can be produced.

Moreover, the pipe member is freely detachably attached to the handle member. Consequently, the pipe member to be inserted into a lumen of a region to be observed can be designed to be disposable.

Incidentally, in the microscopic surgery system, a feeling transmitted to an operator's hand is very important. An operator relies greatly on the feeling. However, the base placement portion 36 of the handle member 33 serving as a hand-held portion has a certain shape. Some operators may find the diameter of the hand-held portion unfit for their hands.

Figure 39A:
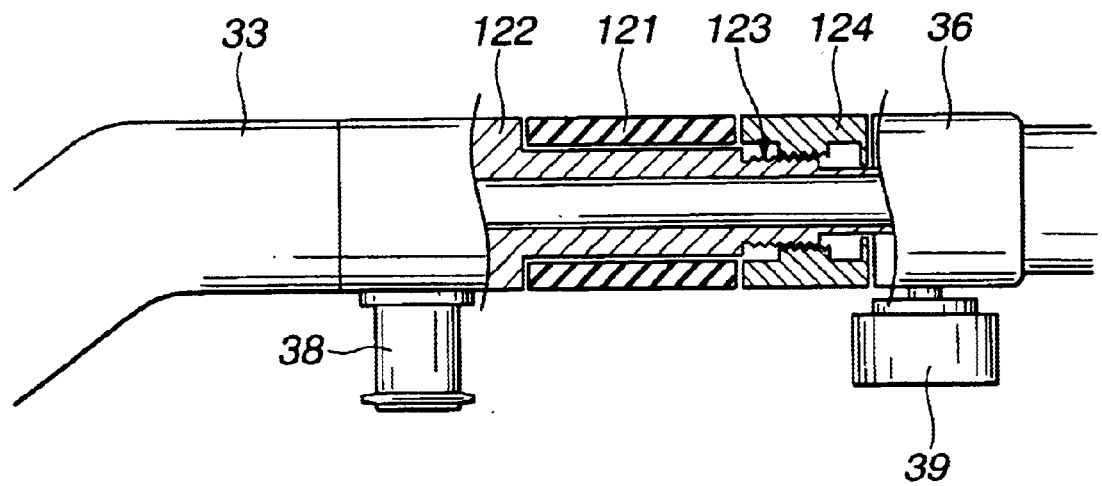
FIG. 39A and FIG. 39B are explanatory diagrams showing a handle member including a hand-held portion whose diameter can be varied depending on the size of an operator's hand.

According to the present embodiment, as shown in FIG. 39A, an elastic member 121 is included in an armor of the base placement portion 36 also serving as a hand-held portion. The elastic member 121 is clamped by a main placement portion 122 and an adjustment knob 124 capable of sliding along a screw 123 threaded on the end of the main placement portion 122.

Figure 39B:
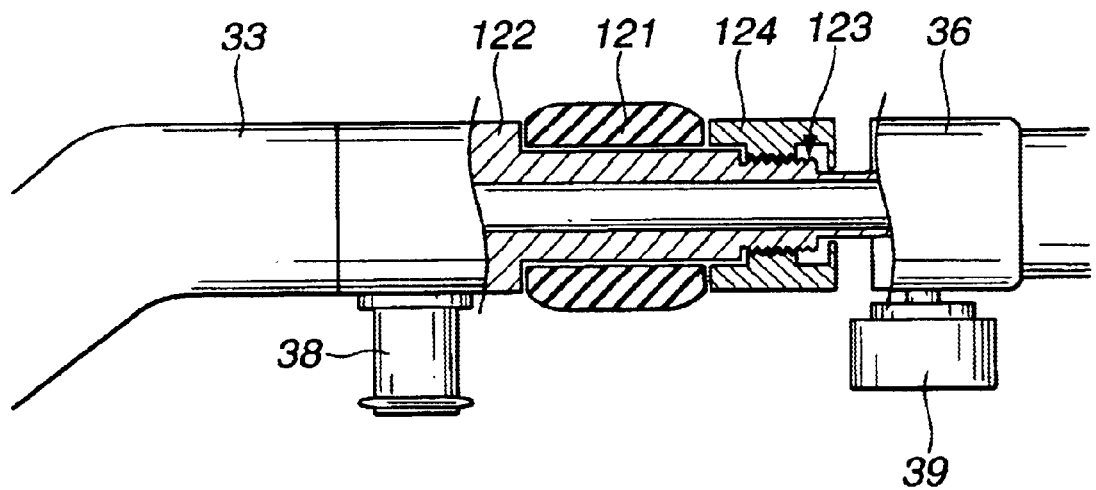

As shown in FIG. 39B, when the adjustment knob 124 is screwed on, the elastic member 121 is crushed due to the adjustment knob 124 and main placement portion 122. This causes the outer diameter of the elastic member 121 to expand. When the adjustment knob 124 is screwed off, the elastic member 121 is restored.

In other words, when the adjustment knob is screwed on or off relative to the main placement portion, the elastic member is dilated or shrunken. Thus, the diameter of the handle member can be made fit for an operator's hand. Consequently, firm holding of the hand-held portion is ensured and maneuverability is improved.

When a tomographic image of a region near a region to be treated is produced, if a brain shift derived from craniotomy is overcome, an ultrasonic image can be superposed on a diagnostic image preoperatively produced through CT or MRI. A structure required for this purpose will be described below.

Figure 40A:
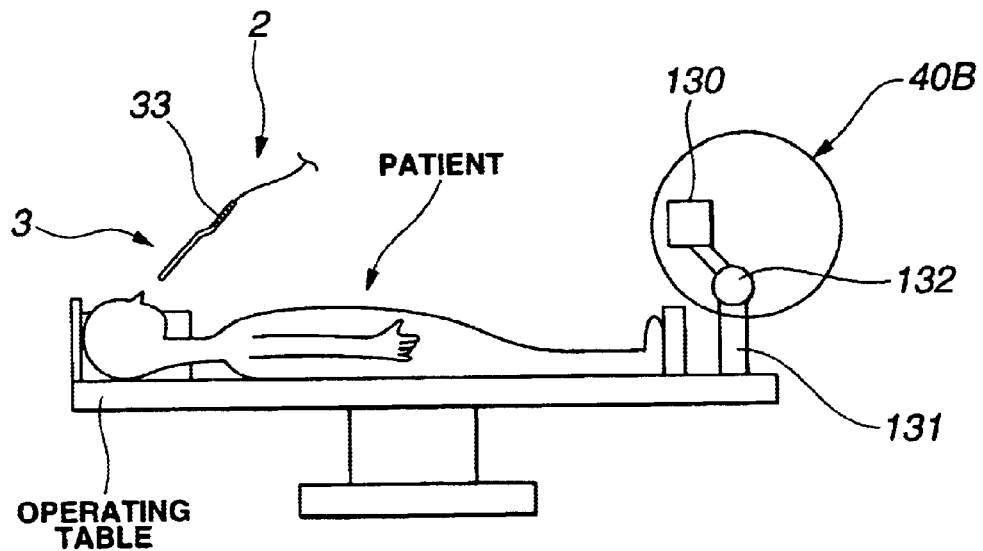
Figure 40B:
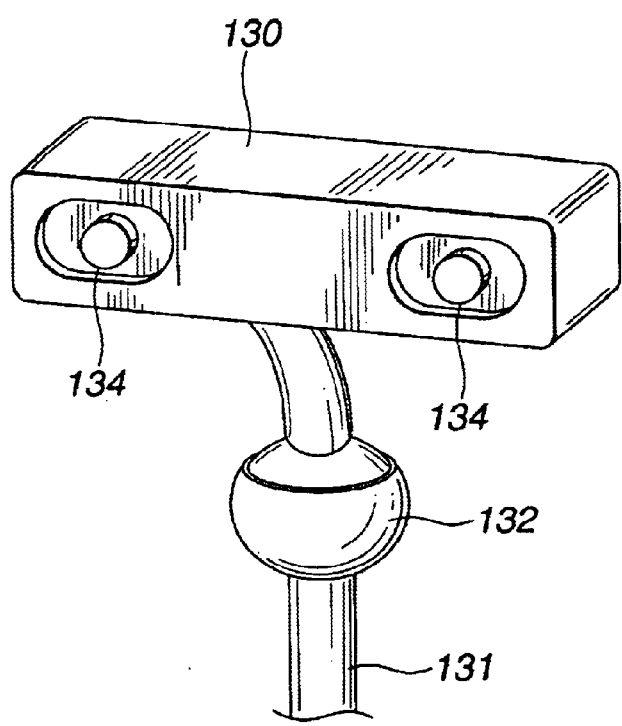

As shown in FIG. 40A and FIG. 40B, a marker member having markers that will be described later is included in the handle member 33 of the observation body 3. Moreover, a navigation body head (hereinafter a body head) having two cameras 134 that follows the marker member is installed at an end of an operating table, on which a patient lies down, near the patient's feet by way of an arm member 131. The arm member 131 has a position adjustment mechanism 132 for adjusting the orientation of the body head 130.

Figure 41:
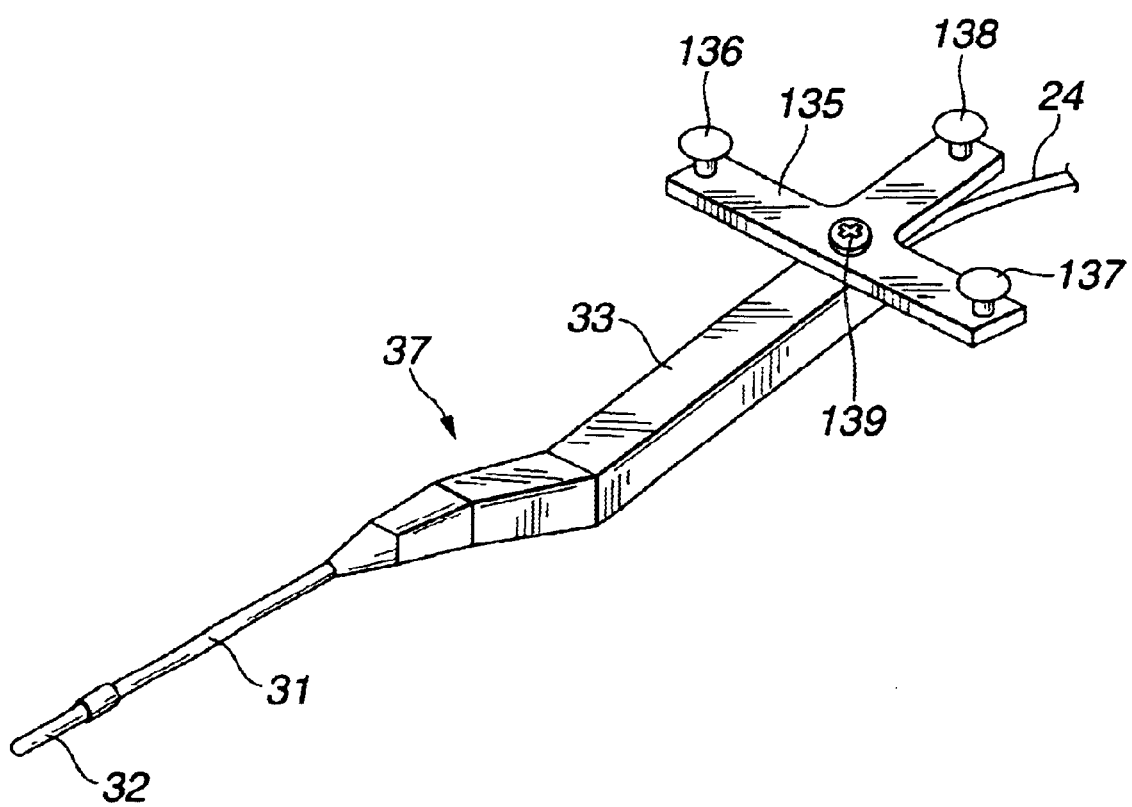

As shown in FIG. 41, a marker member 135 having a first marker 136, a second marker 137, and a third marker 138 arranged thereon is freely detachably attached to the proximal part of the handle member 33 using, for example, a locking screw 139.

Figure 42:
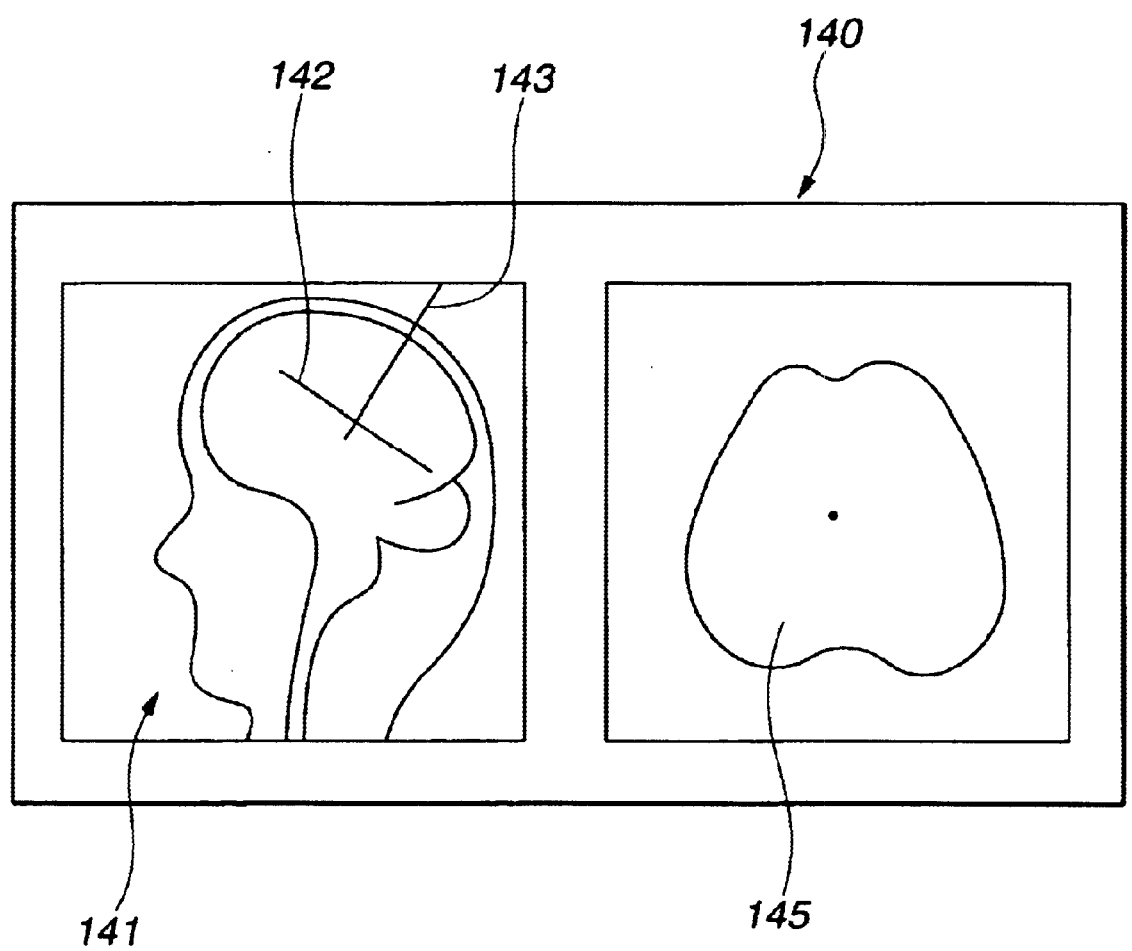

The markers 136, 137, and 138 that move along with the movement of the handle member 33 are followed by the cameras 134. The coordinates representing the positions of the markers 136, 137, and 138 followed by the cameras 134 are arithmetically processed by a CPU included in a position measuring apparatus that is not shown. As shown in FIG. 42, a scanned plane index 142 and a probe index 143 are superimposed on a diagnostic image 141 produced by, for example, MRI and displayed on a screen 140 of a monitor. The scanned plane index 142 expresses the position of a scanned plane represented by an ultrasonic image and calculated through arithmetic operations performed by the CPU. The probe index 143 expresses the direction of insertion of the microscopic probe. An ultrasonic image 145 may be displayed adjacently to the diagnostic image. Consequently, the positional relationship between the ultrasonic probe and a region to be treated can be grasped accurately.

According to the present embodiment, an optical following system having the cameras mounted on the body head is used to measure the position of the handle member. The following system is not limited to the optical type system but may be of a magnetic type or an ultrasonic type.

Surgeons want to ultrasonically observe a lesion deeply located below the observed surface of a region during surgery and perform simple treatment.

According to the present embodiment, therefore, a first gear 151 is fixed to a predetermined point on the flexible shaft 22 that conveys driving torque to the housing 28 accommodating the ultrasonic transducer 29. Moreover, a second gear 152 that meshes with the first gear 151 is fixed to a shaft member 154 supported by a pair of bearings 153. A cutter 155 used to scrape and remove a tumor or the like is fixed together with the second gear 152 onto the shaft member 154. Part of the cutter 155 is bared on the outer surface of the observation body.

Figure 43A:
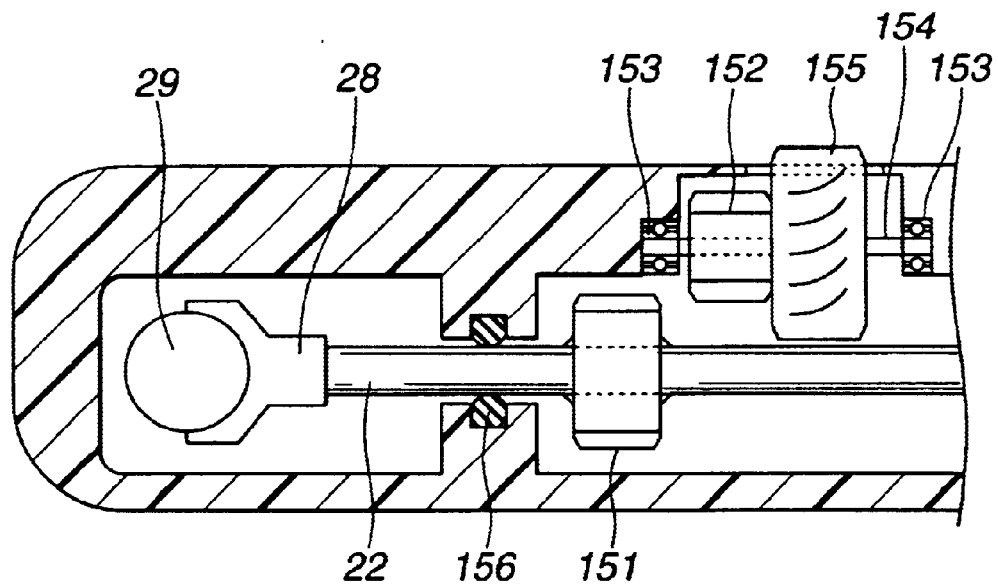
FIG. 43A and FIG. 43B are explanatory diagrams showing an example of a structure included in an ultrasonic probe for microscopic operations having a therapeutic transducer assembly.
Figure 43B:
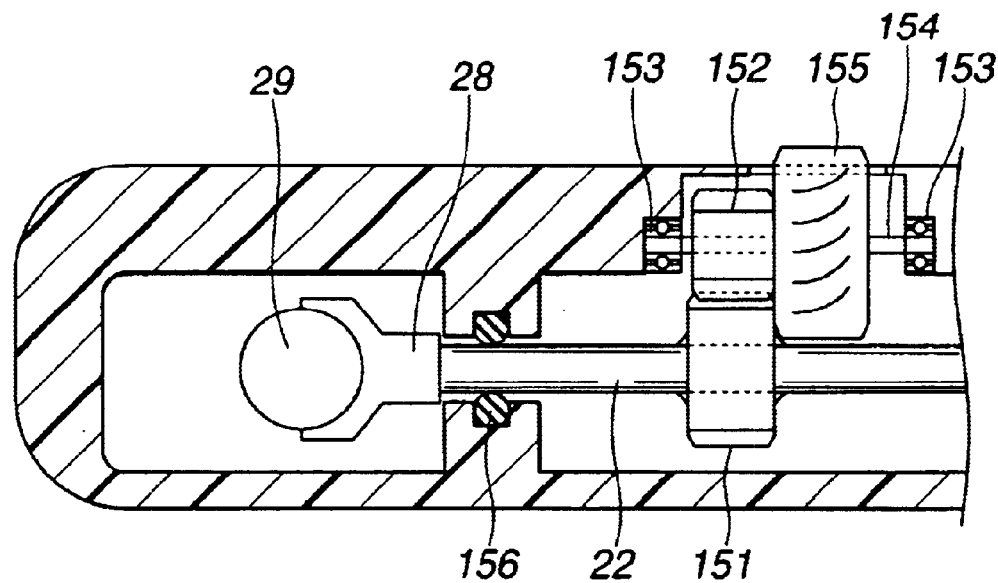

As shown in FIG. 43B, for treating a lesion using the cutter 155, the flexible shaft 22 is withdrawn proximally to cause the first gear 151 to mesh with the second gear 152. The flexible shaft 22 is then rotated. Consequently, driving torque is conveyed to the second gear 152 via the first gear 151. This causes the cutter 155 to rotate to achieve treatment.

Assume that the ultrasonic transducer 29 is rotated in order to perform ultrasonic examination and a tumor or the like is identified on the wall of a lumen. In this case, the flexible shaft 22 is withdrawn proximally by manipulating a specific component formed near an operator's hand in order to mesh the first gear with the second gear 152. The flexible shaft 22 is then rotated. Consequently, the second gear 152 meshed with the first gear 151 is rotated, the shaft member 154 is rotated, and the cutter 155 is rotated. Eventually, the intended tumor or the like can be scraped.

Reference numeral 156 denotes an O ring for holding the flexible shaft 22 and sealing in a watertight manner a clearance around the periphery of the flexible shaft 22.

According to the present invention, it is apparent that a wide range of different embodiments can be constructed based on the invention without a departure from the spirit and scope of the invention. This invention will be limited by the appended claims but not be restricted by any specific embodiments.

What is claimed is:

1. An ultrasonic probe for microscopic operations comprising:
    an ultrasonic probe body having a transducer assembly attached to the distal end of a soft elongated tube that is extended from a connector to be coupled to an ultrasonic observation apparatus, and having a coupler mounted on the tube;
    an elongated tubular member through which said transducer assembly and tube are passed, and a bent handle member attached to the proximal end of said tubular member and includes a coupling mechanism for use in coupling said coupler to the handle member so that said coupler can be uncoupled freely.

2. An ultrasonic probe for microscopic operations usable for cerebral surgery comprising:

an ultrasonic probe body having a transducer assembly attached to the distal end of a soft elongated tube that is extended from a connector to be coupled to an ultrasonic observation apparatus, and having a base member that serves as a coupler mounted on the middle of the tube; and an observation body including a linkage pipe through which said transducer assembly and tube are passed, and a bent handle member that is attached to the proximal end of the linkage pipe and that has a base placement portion serving as a hand-held portion and including a coupling mechanism for use in coupling said base member to the handle member so that said base member can be uncoupled freely.

3. An ultrasonic probe for microscopic operations according to claim 2, wherein said transducer assembly is mechanically driven, and composed of an ultrasonic transducer, a housing that accommodates the ultrasonic transducer, a flexible shaft that has one end thereof coupled to the housing, has the other end coupled to said ultrasonic observation apparatus, and conveys driving torque, and a soft tube member with which the flexible shaft is sheathed.

4. An ultrasonic probe for microscopic operations according to claim 2, wherein: said transducer assembly is electronically driven, and composed of a plurality of transducer elements arranged regularly, and a signal cable having signal lines sheathed with a soft tube member; and the signal lines are extended from the plurality of transducer elements, coupled to said ultrasonic observation apparatus, and used to transmit or receive electric signals.

5. An ultrasonic probe for microscopic operations according to claim 3, wherein: said observation body includes a linkage pipe having an ultrasound transmissive cap, which has a space in which said housing fixed to the distal end of said flexible shaft is placed, attached to the distal end thereof; a pipe placement portion in which the proximal part of the linkage pipe is locked is formed as one end portion of said handle member; and a base placement portion which serves as a hand-held portion and in which said base member is placed is formed as the other end portion of said handle member.

6. An ultrasonic probe for microscopic operations according to claim 3, wherein: said observation body includes a linkage pipe having a distal opening through which said transducer assembly is jutted out; a pipe placement portion in which the proximal part of the linkage pipe is locked is formed as one end portion of said handle member; and a base placement portion which serves as a hand-held portion and in which said base member is placed is formed as the other end portion of said handle member.

7. An ultrasonic probe for microscopic operations according to claim 5, wherein: said observation body includes a pipe placement hollow which is bored in said pipe placement portion and in which the proximal part of said linkage pipe is locked, and a base placement hollow which is bored in said base placement portion and in which said base member is placed; said pipe placement hollow and said base placement hollow have such a positional relationship that the centerlines (axes) thereof are uneven, and are linked by a sloping hollow.

8. An ultrasonic probe for microscopic operations according to claim 6, wherein: said observation body includes a pipe placement hollow which is bored in said pipe placement portion and in which the proximal part of said linkage pipe is locked, and a base placement hollow which is bored in said base placement portion and in which said base member is placed; said pipe placement hollow and said base placement hollow have such a positional relationship that the centerlines (axes) thereof are uneven, and are linked by a sloping hollow.

9. An ultrasonic probe for microscopic operations according to claim 5, wherein said observation body includes a locking member used to lock said base member, which is placed in said base placement hollow, at a predetermined position so that said base member can be unlocked freely.

10. An ultrasonic probe for microscopic operations according to claim 6, wherein said observation body includes a locking member used to lock said base member, which is placed in said base placement hollow, at a predetermined position so that said base member can be unlocked freely.

11. An ultrasonic probe for microscopic operations according to claim 5, wherein at least said ultrasound transmissive cap and handle member are so transparent that their interiors can be discerned.

12. An ultrasonic probe for microscopic operations according to claim 5, wherein said ultrasound transmissive cap included in said observation body is freely detachably attached to said linkage pipe.

13. An ultrasonic probe for microscopic operations according to claim 12, wherein said ultrasound transmissive cap is shaped differently from another ultrasonic transmissive cap so that said ultrasound transmissive cap and another ultrasonic transmissive cap will match different regions to be observed.

14. An ultrasonic probe for microscopic operations according to claim 5, wherein said linkage pipe included in said observation body is a hard pipe shaped straight.

15. An ultrasonic probe for microscopic operations according to claim 6, wherein said linkage pipe included in said observation body is a hard pipe shaped straight.

16. An ultrasonic probe for microscopic operations according to claim 5, wherein said linkage pipe is a shape varying/maintaining pipe capable of being deformed freely and maintaining a changed shape.

17. An ultrasonic probe for microscopic operations according to claim 6, wherein said linkage pipe is a shape varying/maintaining pipe capable of being deformed freely and maintaining a changed shape.

18. An ultrasonic probe for microscopic operations according to claim 14, wherein said straight-shaped hard pipe lies substantially parallel to the centerline (axis) of said base placement portion.

19. An ultrasonic probe for microscopic operations according to claim 15, wherein said straight-shaped hard pipe lies substantially parallel to the centerline (axis) of said base placement portion.

20. An ultrasonic probe for microscopic operations according to claim 14, wherein said straight-shaped hard pipe and the centerline (axis) of said base placement portion meets at an angle $\theta$.

21. An ultrasonic probe for microscopic operations according to claim 14, wherein said straight-shaped hard pipe and the centerline (axis) of said base placement portion meets at an angle $\theta$.

22. An ultrasonic probe for microscopic operations according to claim 5, wherein the weight of said observation body ranges 10 g to 50 g.

23. An ultrasonic probe for microscopic operations according to claim 6, wherein the weight of said observation body ranges 10 g to 50 g.

24. An ultrasonic probe for microscopic operations according to claim 5, the overall length of said observation body ranges from 200 mm to 270 mm.

25. An ultrasonic probe for microscopic operations according to claim 6, the overall length of said observation body ranges from 200 mm to 270 mm.

26. An ultrasonic probe for microscopic operations according to claim 3, wherein said ultrasound transmissive cap has a reflecting mirror surface, which is inclined substantially 45° and realized with an ultrasonic mirror for reflecting ultrasonic waves, opposed to the lateral surface of said rotating ultrasonic transducer.

27. An ultrasonic probe for microscopic operations according to claim 2, wherein a fluid supply channel through which a fluid is supplied and a suction channel through which a fluid is sucked are included in said observation body.

28. An ultrasonic probe for microscopic operations according to claim 2, wherein depth indices used to notify a user of a length of insertion by which said ultrasonic probe has been inserted, and a scanned plane index used to notify a user of the position of a scanned forward plane are marked on said observation body.

29. An ultrasonic probe for microscopic operations according to claim 3, wherein a thick portion that helps orient a distal cap is formed as part of the distal cap linked to the distal end of said handle member.

30. An ultrasonic probe for microscopic operations according to claim 3, wherein a reflector that helps orient said transducer assembly is located in front of the radiating surface of said transducer assembly, or a fluid supply channel or a suction channel is extended to have the distal end thereof located near the distal end of said transducer assembly.

31. An ultrasonic probe for microscopic operations according to claim 4, wherein a reflector that helps orient said transducer assembly is located in front of the radiating surface of said transducer assembly, or a fluid supply channel or a suction channel is extended to have the distal end thereof located near the distal end of said transducer assembly.

32. An ultrasonic probe for microscopic operations according to claim 3, wherein said flexible shaft is composed of flexible shafts having different diameters, and one of the flexible shafts, that is, a small-diameter flexible shaft is passed through said observation body.

* * * * *

UNITED STATES PATENT AND TRADEMARK OFFICE
CERTIFICATE OF CORRECTION

PATENT NO. : 6,641,539 B2
DATED : November 4, 2003
INVENTOR(S) : Kenji Hirooka et al.

It is certified that error appears in the above-identified patent and that said Letters Patent is hereby corrected as shown below:

<u>Title page,</u>
Item [22], insert the following:
-- [30]    Foreign Application Priority Data
Dec. 8, 1999   [JP]   Japan ......................11-349433
Nov. 21, 2000  [JP]   Japan ......................200-354846 --

Signed and Sealed this

Sixteenth Day of March, 2004

JON W. DUDAS
*Acting Director of the United States Patent and Trademark Office*